US012766194B2

(12) United States Patent
Takeda et al.

(10) Patent No.: US 12,766,194 B2
(45) Date of Patent: Oct. 20, 2026

(54) CITRATE-CONTAINING COMPOSITION, PRODUCTION METHOD AND DRY METHOD THEREFOR, AND TABLET CONTAINING SAID COMPOSITION

(71) Applicant: NIPPON CHEMIPHAR CO., LTD., Tokyo (JP)

(72) Inventors: Hideto Takeda, Tokyo (JP); Nozomu Shimazaki, Chikusei (JP)

(73) Assignee: NIPPON CHEMIPHAR CO., LTD., Tokyo (JP)

( * ) Notice: Subject to any disclaimer, the term of this patent is extended or adjusted under 35 U.S.C. 154(b) by 454 days.

(21) Appl. No.: 18/284,411

(22) PCT Filed: Mar. 28, 2022

(86) PCT No.: PCT/JP2022/015012

§ 371 (c)(1),
(2) Date: Sep. 27, 2023

(87) PCT Pub. No.: WO2022/210536

PCT Pub. Date: Oct. 6, 2022

(65) Prior Publication Data

US 2024/0091362 A1 Mar. 21, 2024

(30) Foreign Application Priority Data

Mar. 29, 2021 (JP) ................................ 2021-055436

(51) Int. Cl.

| | |
|---|---|
| ***A61K 41/00*** | (2020.01) |
| ***A61K 31/194*** | (2006.01) |
| ***A61K 47/36*** | (2006.01) |

(52) U.S. Cl.

CPC ............ *A61K 41/00* (2013.01); *A61K 31/194* (2013.01); *A61K 47/36* (2013.01)

(58) Field of Classification Search

CPC ...................................................... A61K 41/00
See application file for complete search history.

(56) References Cited

U.S. PATENT DOCUMENTS

| | | | |
|---|---|---|---|
| 2009/0291944 | A1 | 11/2009 | Ash et al. |
| 2015/0024081 | A1 | 1/2015 | Marcussen et al. |

FOREIGN PATENT DOCUMENTS

| | | | |
|---|---|---|---|
| CA | 3 116 290 | A1 | 4/2020 |
| CA | 3116173 | A1 | 4/2020 |
| CN | 101857543 | A | 10/2010 |
| CN | 103120656 | A | 5/2013 |
| JP | 64-011636 | A | 1/1989 |
| JP | 6-194043 | A | 7/1994 |
| JP | 2003-221362 | A | 8/2003 |
| WO | 2016/159899 | A1 | 10/2016 |

OTHER PUBLICATIONS

Wang et al. CAS: 163: 399070, 2015.*
C. M. McLoughlin et al., "microwave drying of pharmaceutical powders", Food and Bioproducts Processing, 2000, 78(2), pp. 90-96, doi: 10.1205/096030800532798.
C. M. McLoughlin et al., "Microwave Drying of Multi-component Powder Systems", Drying Technology, 2003, 21(2), pp. 293-309, DOI;10.1081/DRT-120017750.
Marianne Popp et al., "Sample preservation for determination of organic compounds: microwave versus freeze-drying", Journal of Experimental Botany, 1996, 47(303), pp. 1469-1473.
International Search Report of PCT/JP2022/015012 dated May 31, 2022 [PCT/ISA/210].
Taiwanese Office Action dated Nov. 4, 2025, issued in Taiwanese application No. 111111945.
Extended European Search Report dated Jan. 24, 2025 in Application No. 22780747.6.
Communication dated Feb. 27, 2026 in Vietnamese Application No. 1-2023-07417.
Chinese Office Action dated Nov. 26, 2025, issued in Chinese application No. 202280025094.0.

* cited by examiner

*Primary Examiner* — Rei Tsang Shiao
(74) *Attorney, Agent, or Firm* — Sughrue Mion, PLLC

(57) ABSTRACT

There is provided a method for producing a composition containing a pharmaceutically acceptable salt of citric acid, a hydrate thereof, or a mixture thereof and having a moisture content of 4.0% by mass or less, the method including irradiating a composition containing a pharmaceutically acceptable salt of citric acid, a hydrate thereof, or a mixture thereof with microwaves.

31 Claims, 2 Drawing Sheets

CITRATE-CONTAINING COMPOSITION, PRODUCTION METHOD AND DRY METHOD THEREFOR, AND TABLET CONTAINING SAID COMPOSITION

CROSS REFERENCE TO RELATED APPLICATIONS

This application is a National Stage of International Application No. PCT/JP2022/015012 filed on Mar. 28, 2022, claiming priority based on Japanese Patent Application No. 2021-055436 filed on Mar. 29, 2021.

TECHNICAL FIELD

The present invention relates to a citrate-containing composition, a production method and a drying method therefor, and a tablet containing the above composition. More specifically, the present invention relates to: a composition containing a pharmaceutically acceptable salt of citric acid or a hydrate thereof, or a mixture thereof and having specific hygroscopic properties; a production method for a composition containing a pharmaceutically acceptable salt of citric acid or a hydrate thereof, or a mixture thereof, and having a moisture content of 4.0% by mass or less, the production method including a step of irradiating a composition containing a pharmaceutically acceptable salt of citric acid or a hydrate thereof, or a mixture thereof, with microwaves; a method for drying the composition including a step of temporarily humidifying the citrate-containing composition, followed by drying; and a tablet containing the composition having specific hygroscopic properties.

Priority is claimed on Japanese Patent Application No. 2021-055436, filed Mar. 29, 2021, the content of which is incorporated herein by reference.

BACKGROUND ART

A citrate-containing composition containing a pharmaceutically acceptable salt of citric acid or a hydrate thereof, or a mixture thereof or the like is known to be useful as a medicament for improving aciduria or acidosis in gout and hyperuricemia, or a pharmaceutical raw material thereof. However, since potassium citrate, for example, exhibits hygroscopicity or deliquescent properties, problems arise, such as deterioration of the storage stability of the composition, and aggregation of raw materials of pharmaceutical preparations during formulation, especially in the production of tablets, to hinder the tableting process.

Conventionally, drying methods using a box type dryer, a fluidized bed dryer, a fluidized bed granulation dryer, or the like are known as methods for drying powder, but drying of the citrate-containing composition is either extremely difficult or inefficient with these conventional methods.

On the other hand, although a microwave drying device is known (Patent Document 1), there is no known example that employs the device for drying the citrate-containing composition.

CITATION LIST

Patent Document

[Patent Document 1] JP H6-194043A

SUMMARY OF INVENTION

Technical Problem

The present invention has been made in view of the above circumstances, and one object of the present invention is to provide an efficient method for drying a citrate-containing composition containing a pharmaceutically acceptable salt of citric acid or a hydrate thereof, or a mixture thereof. Another object of the present invention is to provide an efficient method for producing a citrate-containing composition containing a pharmaceutically acceptable salt of citric acid or a hydrate thereof, or a mixture thereof and having a low moisture content. Yet another object of the present invention is to provide an efficient method for producing a citrate-containing composition containing a pharmaceutically acceptable salt of citric acid or a hydrate thereof, or a mixture thereof and having a low moisture content, using a microwave drying device. Yet another object of the present invention is to provide a citrate-containing composition containing a pharmaceutically acceptable salt of citric acid or a hydrate thereof, or a mixture thereof and having specific hygroscopic properties. Yet another object of the present invention is to provide a tablet containing the citrate-containing composition containing a pharmaceutically acceptable salt of citric acid or a hydrate thereof, or a mixture thereof and having specific hygroscopic properties.

Solution to Problem

As a result of intensive studies in order to achieve the objects described above, the inventors of the present invention have found that: a composition containing a pharmaceutically acceptable salt of citric acid or a hydrate thereof, or a mixture thereof and having a moisture content of 4.0% by mass or less can be produced efficiently by irradiating a citrate-containing composition obtained by mixing a pharmaceutically acceptable salt of citric acid or a hydrate thereof, or a mixture thereof, that are placed in a normal state, with microwaves; and that the composition obtained by the production method has specific hygroscopic properties. In addition, the inventors of the present invention have found that the citrate-containing composition can be dried efficiently by temporarily humidifying the citrate-containing composition, followed by drying. Furthermore, the inventors of the present invention have found that: by producing a tablet using the citrate-containing composition having specific hygroscopic properties, no problem arises in the tablet production; and that the produced tablet has excellent characteristics as a tablet, thereby completing the present invention.

That is, the present invention includes the following aspects.

(1) A production method for a composition containing a pharmaceutically acceptable salt of citric acid or a hydrate thereof, or a mixture thereof and having a moisture content of 4.0% by mass or less, the production method including a step of irradiating a composition containing a pharmaceutically acceptable salt of citric acid, a hydrate thereof, or a mixture thereof with microwaves;

(2) The production method according to (1), further including a step of controlling a temperature and relative humidity of an environment in which the composition containing a pharmaceutically acceptable salt of citric acid or a hydrate thereof, or a mixture thereof is placed;

(3) The production method according to (1) or (2), wherein the pharmaceutically acceptable salt of citric acid or the hydrate thereof, or the mixture thereof is potassium citrate or a hydrate thereof, sodium citrate or a hydrate thereof, or a mixture thereof;

(4) The production method according to any one of (1) to (3), wherein the pharmaceutically acceptable salt of citric acid or the hydrate thereof, or the mixture thereof is potassium citrate monohydrate ($C_6H_5K_3O_7 \cdot H_2O$), sodium citrate dihydrate ($C_6H_5Na_3O_7 \cdot 2H_2O$), or a mixture thereof;

(5) The production method according to any one of (2) to (4), wherein the step of controlling the temperature and relative humidity include, provision of a first section in which a temperature of the composition irradiated with the microwaves is controlled so that the relative humidity is 80% RH or higher and 100% R H or lower from start of the irradiation with the microwaves;

(6) The production method according to (5), wherein the step of controlling the temperature and relative humidity includes provision of a second section in which the relative humidity is controlled to 10% RH or higher and 90% RH or lower after passing through the first section;

(7) The production method according to (5) or (6), wherein the first section is controlled to be 50° C., or higher and 80° C., or lower;

(8) The production method according to any one of (1) to (7), wherein a temperature of the composition irradiated with the microwaves is 90° C., or higher and lower than 175° C.;

(9) The production method according to any one of (1) to (8), wherein a temperature of the composition irradiated with the microwaves is 100° C., or higher and 120° C., or lower;

(10) The production method according to any one of (1) to (9), wherein a temperature of the composition irradiated with the microwaves is 110° C.;

(11) The production method according to any one of (1) to (10), wherein an output of the microwaves is 0.05 kW/kg or more and 2 kW/kg or less;

(12) The production method according to any one of (1) to (11), wherein the composition further contains an additive;

(13) The production method according to any one of (1) to (12), wherein the composition further contains anhydrous citric acid;

(14) The production method according to any one of (1) to (13), wherein the composition further contains partially pregelatinized starch;

(15) The production method according to any one of (1) to (14), further including:

a) a step of preparing a composition obtained by mixing the pharmaceutically acceptable salt of citric avid or a hydrate thereof, or a mixture thereof, and optionally another component, that are placed in a normal state;

b) a step of placing the composition on a conveying means in a microwave drying device;

c) a step of conveying the composition placed on the conveying means to a microwave irradiation chamber provided in the microwave drying device; and d) a step of continuously irradiating the composition conveyed to the microwave irradiation chamber with microwaves,

(16) The production method according to (15), wherein e) the step of preparing the composition includes mixing by a mixer; and f) the step of placing on a conveying means includes conveyance by blowing air into a pipe connecting the mixer and the microwave drying device:

(17) The production method according to (15) or (16), wherein controlling of the relative humidity is performed by opening and/or closing an exhaust port provided in the microwave irradiation chamber;

(18) The production method according to any one of (1) to (4), (8), and (12) to (14), including:

a) a step of preparing a composition obtained by mixing the pharmaceutically acceptable salt of citric acid or a hydrate thereof, or a mixture thereof, and optionally another component, that are placed in a normal state;

b1) a step of placing the composition in a microwave reduced pressure drying device; and c1) a step of irradiating the placed composition with microwaves;

(19) The production method according to (18), wherein controlling of the relative humidity is performed by a pressure reducing means provided in the microwave reduced pressure drying device;

(20) A drying method for a composition containing a pharmaceutically acceptable salt of citric acid, a hydrate thereof, or a mixture thereof by heating, the drying method including: a step of controlling a temperature and relative humidity of an environment in which the composition is placed to temporarily increase a moisture content of the composition at an initial stage of the heating;

(21) The drying method according to (20), wherein the pharmaceutically acceptable salt of citric acid or the hydrate thereof, or the mixture thereof is potassium citrate or a hydrate thereof sodium citrate or a hydrate thereof, or a mixture thereof;

(22) The drying method according to (20) or (21), wherein the pharmaceutically acceptable salt of citric acid or the hydrate thereof, or the mixture thereof is potassium citrate monohydrate ($C_6H_5K_3O_7 \cdot H_2O$), sodium citrate dihydrate ($C_6H_5Na_3O_7 \cdot 2H_2O$), or a mixture thereof;

(23) The drying method according to any one of (20) to (22), wherein a method of the heating is a method by heat radiation, heat conduction or heat transfer from a heat source, and the temperature of the environment at the initial stage of the heating is 50° C. or higher and 65° C., or lower, and the relative humidity is 45% RH or higher and 60% RH or lower;

(24) The drying method according to any one of (20) to (23), including a step of maintaining the temperature and relative humidity of the environment at the initial stage of the heating after temporarily increasing the moisture content of the composition;

(25) The drying method according to any one of (20) to (22), wherein a method of the heating is a method of radiant heating by microwave irradiation, and the temperature of the environment at the initial stage of the heating is 50° C., or higher and 80° C., or lower, and the relative humidity is 80% RH or higher and 100% RH or lower;

(26) The drying method according to (25), including a step of controlling the temperature of the environment in which the composition is placed to 90° C., or higher and lower than 175° C., and the relative humidity to 10% RH or higher and 90%. RH or lower after temporarily increasing the moisture content of the composition;

(27) A microwave irradiated composition containing a pharmaceutically acceptable salt of citric acid or a hydrate thereof, or a mixture thereof, wherein the composition has a characteristic that when the composition is stored in an environment at a temperature of 25° C., and a relative humidity of 75% RH, a moisture content 10 days after the end of the irradiation is 1.5 times or less a moisture content 2 days after the end of the irradiation;

(28) The composition according to (27), wherein the pharmaceutically acceptable salt of citric acid or the hydrate thereof, or the mixture thereof is potassium citrate or a hydrate thereof, sodium citrate or a hydrate thereof, or a mixture thereof

(29) The composition according to (26) or (28), wherein the pharmaceutically acceptable salt of citric acid or the hydrate thereof, or the mixture thereof is potassium citrate monohydrate ($C_6H_5K_3O_7{\cdot}H_2O$)), sodium citrate dihydrate ($C_6H_5Na_3O_7{\cdot}2H_2O$), or a mixture thereof;

(30) A tablet containing the composition according to any one of (27) to (29); and

(31) A method for producing a composition containing a pharmaceutically acceptable salt of citric acid or a hydrate thereof, or a mixture thereof, and in which a total content of the composition does not exceed 100% by mass with respect to a total mass of solid content of the composition, the production method including a step of irradiating a composition containing a pharmaceutically acceptable salt of citric acid, a hydrate thereof, or a mixture thereof with microwaves.

Effects of Invention

According to the present invention, it is possible to provide: an efficient method for producing a citrate-containing composition containing a pharmaceutically acceptable salt of citric acid or a hydrate thereof, or a mixture thereof, and having a low moisture content; a citrate-containing composition having specific hygroscopic properties; an efficient method for drying a citrate-containing composition; and a tablet containing the citrate-containing composition having specific hygroscopic properties.

DESCRIPTION OF EMBODIMENTS

Figure 1:
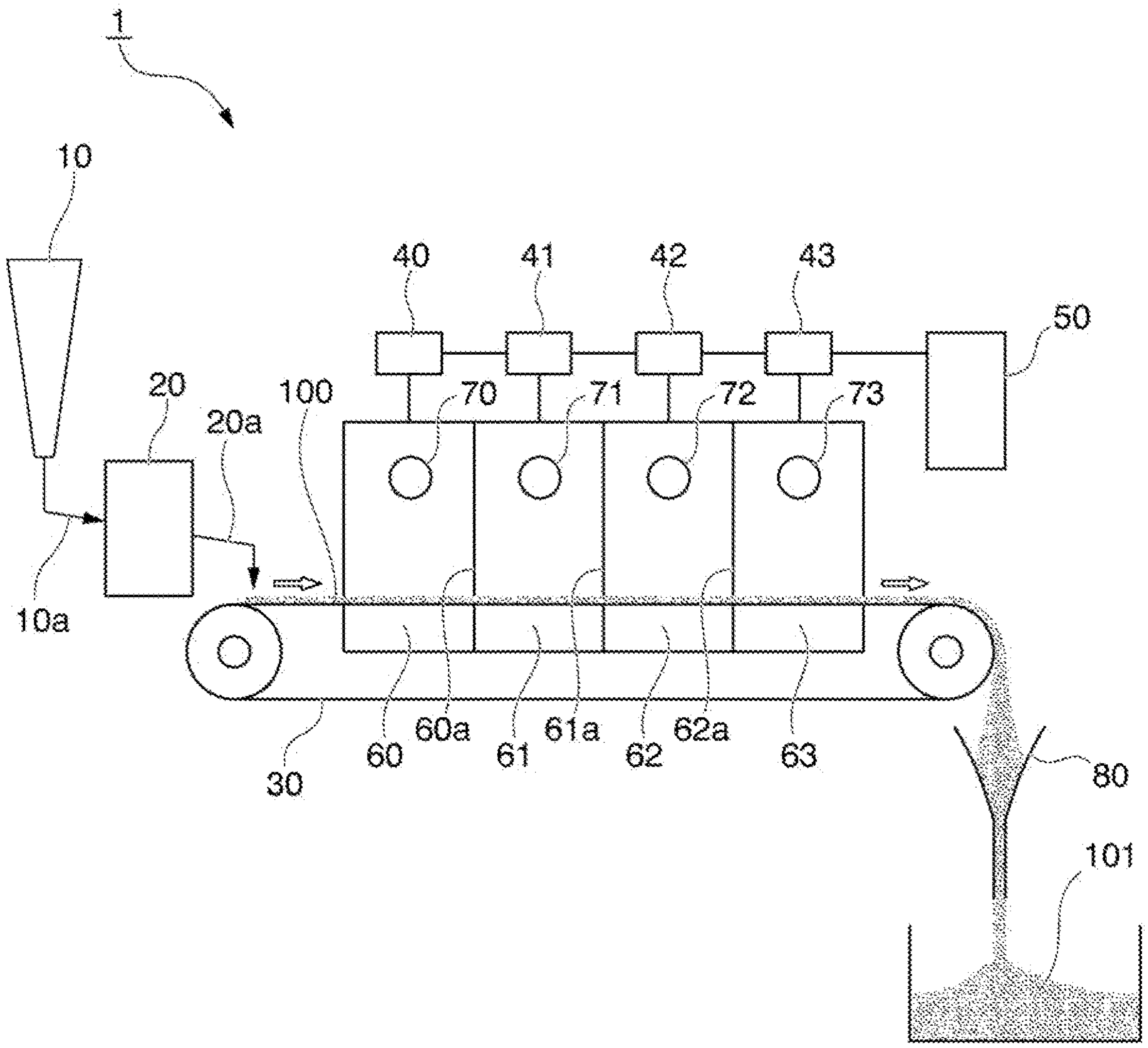
FIG. 1 is a schematic diagram of a microwave drying device applied to one embodiment of a production method of the present invention.

Next, the present invention will be described in further detail.

In the present specification, examples of the "pharmaceutically acceptable salt of citric acid" include alkali metal salts of citric acid. Examples of the alkali metal salt of citric acid include potassium citrate and sodium citrate, and may each be a stable hydrate such as a monohydrate of potassium citrate ($C_6H_5K_3O_7{\cdot}H_2O$) and a dihydrate of sodium citrate ($C_6H_5Na_3O_7{\cdot}2H_2O$).

In the present specification, the term "potassium citrate" means "tripotassium citrate ($C_6H_5K_3O_7$)", and the term "sodium citrate" means "trisodium citrate ($C_6H_5Na_3O_7$)". Therefore, potassium citrate monohydrate is represented by a composition formula: $C_6H_5K_3O_7{\cdot}H_2O$, and sodium citrate dihydrate is represented by a composition formula $C_6H_5Na_3O_7{\cdot}2H_2O$.

The "moisture content" is expressed as a percentage by mass as the content of moisture with respect to the mass of the entire composition that may contain that moisture. When the above composition contains a hydrate, the above moisture content may be an amount that includes water of crystallization of this hydrate. The above moisture content can be measured, for example, by a heating and drying type moisture meter (for example, using MX-50 (manufactured by A & D Co., Ltd.) under automatic stop conditions of 5 g/180° C., and ending the measurement when reaching 0.05%/min or less), or can be measured by a Karl Fischer method (coulometric titration method or volumetric titration method), a simultaneous thermogravimetric-differential thermal analyzer (TG-DTA), a differential scanning calorimeter (DSC), a thermogravimetric analysis (TGA), and the like.

Unless otherwise specified, the "total mass of solid content of the composition" refers to the mass obtained by subtracting the mass of components that are liquid in a normal state, such as moisture, from the total mass of the above composition (provided that when a component of the composition contains water of crystallization, the mass of the water of crystallization is included in the mass of the solid content).

The term "microwave" means an electromagnetic wave with a frequency of about 300 MHz to 30 GHz (wavelength of 1 m to 1 cm), and the frequency is preferably from 2,400 to 2,500 MHz, and more preferably 2,450±30 MHz. Further, the output of the microwave, as a set output of a microwave irradiation unit, is preferably 2 kW or more and 24 kW or less, more preferably 2 kW or more and 12 kW or less, still more preferably 2 kW or more and 6 kW or less, and still more preferably 4 kW or more and 6 kW or less. In addition, considering the mass of an object to be irradiated with microwaves, the output of microwaves can also be expressed as a physical quantity per unit mass of the object to be irradiated. When expressed in terms of output per unit mass of the object to be irradiated, the microwave output may be 2 kW/kg or less, preferably 1 kW/kg or less, and more preferably 0.5 kW/kg or less. Although the lower limit value of the microwave output is not particularly limited, for example, if it is 0.05 kW/kg or mom, the moisture content of the object to be irradiated can be efficiently reduced. Therefore, the microwave output is preferably 0.05 kW/kg or more and 2 kW/kg or less, more preferably 0.2 kW/kg or more and 2 kW/kg or less, sill more preferably 0.2 kW/kg or mom and 1 kW/kg or less, still more preferably 0.24 kW/kg or more and 1 kW/kg or less, and still more preferably 0.24 kW/kg or more and 0.5 kW/kg or less.

The expression "normal state" means an environment of about 1 atmosphere (that is, 86 kPa or more and 106 kPa or less), "normal temperature" and "normal humidity", and the term "normal temperature" means 5 to 35° C. (sometimes referred to as room temperature), and the term "normal humidity" means an environment with a relative humidity of 45 to 85% RH. It should be noted that in the "normal state", if a stricter standard is required, an environment of atmospheric pressure of 101.3 kPa, temperature of 20° C., and relative humidity of 65% would be applied.

The “temperature of the composition” typically represent-s the surface temperature of the composition.

For example, the expression [A, B and/or C] means “at least one selected from the group consisting of A, B and C”.

<Citrate-Containing Composition>

A citrate-containing composition according to the present invention contains a pharmaceutically acceptable salt of citric acid, a hydrate thereof, or a mixture thereof, preferably potassium citrate or a hydrate thereof, sodium citrate or a hydrate thereof, or a mixture thereof, and the potassium citrate is preferably a monohydrate thereof ($C_6H_5K_3O_7 \cdot H_2O$), and the sodium citrate is preferably a dihydrate thereof ($C_6H_5Na_3O_7 \cdot 2H_2O$).

A mixing ratio of potassium citrate or a hydrate thereof and sodium citrate or a hydrate thereof, preferably a monohydrate of potassium citrate and a dihydrate of sodium citrate, can be appropriately set by those skilled in the art. For example, the molar ratios of potassium citrate monohydrate and sodium citrate dihydrate may be from 0.05:1.95 to 1.95:0.05, from 0.1:1.9 to 1.9:0.1, from 0.25:1.75 to 1.75:0.25, from 0.5:1.5 to 1.5:0.5, from 035:1.25 to 1.25:0.75, from 0.85:1.15 to 1.15:0.85, from 0.90:1.10 to 1.10:0.90, from 0.95:1.05 to 1.05:0.95, or from 0.99:1.01 to 1.01:0.99, and preferably 1:1.

The citrate-containing composition may further contain citric acid, preferably anhydrous citric acid. When citric acid, preferably anhydrous citric acid, is contained, a mixing ratio of citric acid, potassium citrate or a hydrate thereof, and sodium citrate or a hydrate thereof, preferably a mixing ratio of anhydrous citric acid, potassium citrate monohydrate and sodium citrate dihydrate can be appropriately set by those skilled in the art, and for example, it may be 1:0.05 to 0.2:3.8 to 3.95, 1:0.1 to 0.25:3.75 to 3.9, 1:0.25 to 0.5:3.5 to 3.75, 1:0.5 to 0.75:3.25 to 3.5, 1:0.75 to 1.0:3.25 to 3.0, 1:10 to 1.5:2.5 to 3.0, 1:1.5 to 1.8:2.2 to 2.5, 1:1.7 to 2.3:1.7 to 2.3, 1:1.9 to 2.1:1.9 to 2.1 or 1:1.95 to 2.05:1.95 to 2.05, and preferably 1:2:2.

In one embodiment, the citrate-containing composition may have a mixing ratio of citric acid, potassium citrate or a hydrate thereof, and sodium citrate or a hydrate thereof, preferably a mixing ratio of anhydrous citric acid, potassium citrate monohydrate and sodium citrate dihydrate, of, for example, 1:0.05 to 0.2:3.8 to 3.95, 1:0.1 to 0.25:3.75 to 3.9, 1:0.25 to 0.5:3.5 to 3.75, 1:0.5 to 0.75:3.25 to 3.5, 1:0.75 to 1.0:3.25 to 3.0, 1:1.0 to 1.5:2.5 to 3.0, 1:1.5 to 1.8:2.2 to 2.5, 1:1.7 to 2.3:1.7 to 2.3, 1:1.9 to 2.1:1.9 to 2.1 or 1:1.95 to 2.05:1.95 to 2.05, and preferably 1:2:2.

In one embodiment, the sum of the contents of potassium citrate or a hydrate thereof and sodium citrate or a hydrate thereof, preferably potassium citrate monohydrate and sodium citrate dihydrate, is from 10 to 100% by mass, preferably from 50 to 100% by mass, more preferably from 60 to 100% by mass, still more preferably from 75 to 100% by mass, and particularly preferably from 78 to 88% by mass with respect to the total mass of solid content of the citrate-containing composition.

In one embodiment, the moisture content of the undried citric acid-containing composition, that is, the moisture content of the undried composition of citric acid, potassium citrate or a hydrate thereof, and sodium citrate or a hydrate thereof, preferably the composition of anhydrous citric acid, potassium citrate monohydrate and sodium citrate dihydrate, is usually 8.0% by mass or more, and depending on the storage conditions and the humidity in the storage environment, may be 7.5% by mass or more, and at least 6.0% by mass. In the present specification, the moisture content of the undried citric acid-containing composition is expressed, for example, as a normal moisture content of the undried composition of anhydrous citric acid, potassium citrate monohydrate and sodium citrate dihydrate, and may be, for example, from 6.0 to 12.0% by mass, from 7.5 to 11.0% by mass, from 7.5 to 10.0% by mass, or from 7.5 to 8.5% by mas.

The above citrate-containing composition may further contain an additive, preferably a pharmaceutically acceptable additive. Examples of such an additive include an excipient, a binder, a disintegrant, a fluidizer, a flavoring agent, a lubricant, a pH adjuster, a surfactant and a stabilizer, and the like known per se in the technical field of pharmaceutical preparation.

Examples of the above excipient include sugars such as lactose (for example, lactose hydrates and anhydrous lactose), glucose, sucrose, fructose, and maltose, sugar alcohols such as erythritol, sorbitol, maltitol, xylitol, and D-mannitol starches (for example, corn starch, potato starch, rice starch, and wheat starch), crystalline cellulose, magnesium aluminometasilicate, anhydrous calcium phosphate, precipitated calcium carbonate, calcium silicate, calcium lactate and ethyl cellulose, and crystalline cellulose is particularly preferred.

The content of the above excipient may be front 1 to 10% by mass, and preferably from 3 to 7% by mass, with respect to the total mass of the solid content of the citrate-containing composition.

Examples of the above binder include hydroxypropyl cellulose, hydroxypropyl methylcellulose, polyvinylpyrrolidone, dextrin, methyl cellulose, polyvinyl alcohol, sodium alginate, aminoalkyl methacrylate copolymers, polyethylene glycol, pregelatinized starch (for example, partially pregelatinized starch), agar and gelatin, and hydroxypropyl cellulose is particularly preferred.

The content of the above binder may be from 0.1 to 1% by mass, and preferably from 0.2 to 0.8% by mass, with respect to the total mass of the solid content of the citrate-containing composition.

Examples of the above disintegrant include croscarmellose sodium, carmellose calcium, sodium carboxymethyl starch, low-substituted hydroxypropyl cellulose, crospovidone, starches (for example, wheat starch, corn starch, and partially pregelatinized starch) and carmellose, and partially pregelatinized starch is particularly preferred.

The content of the above disintegrant may be from 0.3 to 20% by mass, preferably from 1 to 10% by mass, and more preferably from 3 to 7% by mass, with respect to the total mass of the solid content of the citrate-containing composition.

Examples of the above fluidizer include light anhydrous silicic acid, talc, and magnesium aluminometasilicate.

The content of the above fluidizer may be from 0.03 to 3% by mass, preferably from 0.1 to 3% by mass, and more preferably from 0.3 to 3% by mass, with respect to the total mass of the solid content of the citrate-containing composition.

Examples of the above flavoring agent include acidulants such as malic acid, acetic acid, tartaric acid, fumaric acid and ascorbic acid, and sweeteners such as sodium saccharin, dipotassium glycyrrhizinate, aspartame (registered trademark), stevia, thaumatin and sucralose.

The content of the above flavoring agent may be from 0.03 to 3% by mass, preferably from 0.1 to 3% by mass, and more preferably from 0.3 to 3% by mass, with respect to the total mass of the solid content of the citrate-containing composition.

Examples of the above lubricant include magnesium stearate, calcium stearate, tale, light anhydrous silicic acid, sucrose fatty acid esters, carnauba wax, macrogol and sodium stearyl fumarate, and magnesium stearate is particularly preferred.

The content of the above lubricant may be from 0.1 to 10% by mass, preferably from 0.3 to 5% by mass, and more preferably from 0.5 to 3% by mass, with respect to the total mass of the solid content of the citrate-containing composition.

Examples of the above pH adjuster include citric acid, phosphates (for example, sodium dihydrogen phosphate and potassium dihydrogen phosphate), carbonates (for example, magnesium carbonate and sodium carbonate), tartrates, fumarates, acetates and amino acid salts (provided that the above pH adjuster is not included in the active ingredients according to the present invention).

The content of the above pH adjuster may be from 0.1 to 30% by mass, preferably from 0.3 to 10% by mass, and more preferably from 1 to 5% by mass, with respect to the total mass of the solid content of the citrate-containing composition.

Examples of the above surfactant include sodium lauryl sulfate, polysorbate, sucrose fatty acid esters, polyoxyethylene hydrogenated castor oil, polyoxyl stearate, macrogol and poloxamer.

The content of the above surfactant may be from 0.01 to 3% by mass, preferably from 0.03 to 1% by mass, and more preferably from 0.03 to 0.5% by mass, with respect to the total mass of the solid content of the citrate-containing composition.

Examples of the above stabilizer include anhydrous citric acid, malic acid, acetic acid, tartaric acid, maleic acid, ascorbic acid, sodium edetate, and tocopherol.

The content of the above stabilizer may be from 0.01 to 30% by mass, preferably from 0.1 to 30% by mass, and more preferably from 1 to 20% by mass, with respect to the total mass of the solid content of the citrate-containing composition.

The total content of citric acid, preferably anhydrous citric acid, potassium citrate or a hydrate thereof, and sodium citrate or a hydrate thereof, preferably the total content of anhydrous citric acid, potassium citrate monohydrate, sodium citrate dihydrate, and the above additive, in the citrate-containing composition according to the present invention, does not exceed 100% by mass with respect to the total mass of the solid content of the citrate-containing composition.

As the above additive, an excipient, a binder, a disintegrant, a stabilizer, a lubricant and the like are preferred.

In one embodiment, the citrate-containing composition may be composed only of potassium citrate monohydrate and sodium citrate dihydrate, and may be composed only of anhydrous citric acid, potassium citrate monohydrate and sodium citrate dihydrate.

In one embodiment, the citrate-containing composition obtained by the production method described below or the citrate-containing composition to which the drying method described below is applied may be the citrate-containing composition having specific hygroscopic properties.

One aspect of the present invention is a microwave irradiated composition containing a pharmaceutically acceptable salt of citric acid or a hydrate thereof, or a mixture thereof, preferably a composition containing potassium citrate monohydrate and sodium citrate dihydrate, wherein the composition has a characteristic that when the composition is stored in an environment at a temperature of 25° C. and a relative humidity of 75% RH, the moisture content 10 days after the end of the irradiation is 1.5 times or less the moisture content 2 days after the end of the irradiation.

In one embodiment, the moisture content of the composition 10 days after the end of the irradiation is 1.5 times or less, preferably 1.3 times or less, more preferably 1.2 times or less, still more preferably 1.1 times or less, and particularly preferably 1.05 times or less, the moisture content 2 days after the end of the irradiation. In addition, the lower limit value of the ratio of the moisture content 10 days after the end of the irradiation and the moisture content 2 days after the end of the irradiation may be usually 1.0 times.

Due to such hygroscopic properties, the storage stability is excellent, and in formulation, especially in tablet production, it is possible to suppress the aggregation of raw materials of pharmaceutical preparations without causing problems in tableting.

<Production Method>

In one embodiment, the present invention provides a method for producing a composition containing a pharmaceutically acceptable salt of citric acid or a hydrate thereof, or a mixture thereof, preferably potassium citrate monohydrate and sodium citrate dihydrate, and having a moisture content of 4.0% by mass or less, the method including a step of irradiating, with microwaves, a composition containing a pharmaceutically acceptable salt of citric acid or a hydrate thereof, or a mixture thereof, preferably potassium citrate monohydrate and sodium citrate dihydrate, and having a normal moisture content (moisture content is, for example, from 6.0 to 12.0% by mass, front 7.5 to 11.0% by mass, from 7.5 to 10.0% by mass, or from 7.5 to 8.5% by mass, and preferably from 7.5 to 8.5% by mass).

The composition containing a pharmaceutically acceptable salt of citric acid or a hydrate thereof, or a mixture thereof, preferably potassium citrate monohydrate and sodium citrate dihydrate, and having a normal moisture content (moisture content is, for example, from 6.0 to 12.0% by mass, from 7.5 to 11.0% by mass, from 7.5 to 10.0% by mass, or from 7.5 to 8.5% by mass, and preferably from 7.5 to 8.5% by mass) (hereinafter sometimes referred to as a raw material composition) can be prepared by mixing a pharmaceutically acceptable salt of citric acid, a hydrate thereof, or a mixture thereof, preferably potassium citrate monohydrate and sodium citrate dihydrate, and, if desired, anhydrous citric acid and/or the above additive in a normal state. The state of the raw material composition having a normal moisture content is a moisture content with respect to the total mass of the raw material composition, which can be obtained by preparation in a normal state.

Mixing of a pharmaceutically acceptable salt of citric acid or a hydrate thereof, or a mixture thereof, preferably potassium citrate monohydrate and sodium citrate dihydrate, and, if desired, anhydrous citric acid and/or the above additive is not particularly limited as long as it does not adversely affect the present invention. For the above mixing, for example, a V-type mixer, a W-type mixer, a drum-type mixer, a ribbon mixer, a conical screw-type mixer, and the like known per se can be used, and among them, a V-type mixer can be suitably used.

In one embodiment, the mixing is carried out by charging each component of the above raw material composition into a V-type mixer, and mixing for 5 to 20 minutes, preferably 8 to 12 minutes, at a rotational frequency of 10 to 30 ($min^{-1}$), preferably 17 to 23 ($min^{-1}$). The order of adding each component is not particularly limited.

In the present invention, the raw material composition is preferably provided in the form of a powder, and the raw material composition is preferably pulverized and/or classified before and/or after the mixing, preferably after the mixing.

For the above pulverization and/or classification, a pulverizer and/or a classifier (for example, ACM pulverizer (ACM-15H); manufactured by Hosokawa Micron Corporation) can be used, and the average particle size D50 of the powder of the raw material composition is preferably 100 μm or less, more preferably 50 μm or less, still more preferably 30 μm or less, still more preferably 20 μm or less, and most preferably 10 μm or less. The average particle size can be measured by the Analytical Sieving Method (The Japanese Pharmacopoeia, 17th Edition, General Tests, Processes and Apparatus).

Subsequently, by irradiating the raw material composition with microwaves, the moisture content of the raw material composition is adjusted to 4.0% by mass or less, and the target composition containing a pharmaceutically acceptable salt of citric acid or a hydrate thereof, or a mixture thereof, preferably potassium citrate monohydrate and sodium citrate dihydrate, and having a moisture content of 4.0% by mass or less, preferably from 0.0 to 3.0% by mass, more preferably from 0.5 to 2.5% by mass, still more preferably from 0.7 to 2.0% by mass, and most preferably from 0.7 to 1.7% by mass, can be obtained.

The composition containing a pharmaceutically acceptable salt of citric acid, a hydrate thereof, or a mixture thereof, preferably potassium citrate monohydrate and sodium citrate dihydrate and having a moisture content of 4.0% by mass or less, obtained by the production method of the present invention, may be a substance having not only the raw material composition of a low moisture content, but also having at least different physicochemical properties such as water absorption properties (sometimes referred to as hygroscopic properties) from those of the raw material composition, as described above. When placed in an environment with a constant relative humidity, the raw material composition mixed in a normal state absorbs moisture in the environment. However, when the composition obtained by the production method of the present invention is placed under the same environment as that of the raw material composition, its water absorption rate and absorption speed tend to be lower than those of the raw material composition.

In the above microwave irradiation, the powder of the raw material composition is preferably deposited so as to form a layer of about 3 cm (for example, from 2.0 to 3.5 cm) and irradiated with microwaves. By doing so, the entire raw material composition can be efficiently irradiated with microwaves, and the moisture content of the raw material composition can be efficiently reduced. Therefore, in one embodiment, when the production method of the present invention is carried out by a batch system, the amount of raw material composition that can be subjected to a single production operation may be limited to such an amount that the above layer of about 3 cm of the raw material composition can be uniformly irradiated with microwaves. However, in another embodiment, when the production method of the present invention is carried out by a continuous system, for example, by providing a plurality of microwave irradiation units in a row and conveying the raw material composition placed as a layer of about 3 cm on a conveying means such as a belt conveyor, the raw material composition can be continuously added while being irradiated with microwaves emitted from the above microwave irradiation units installed in a row.

The microwave drying device used in the above batch system may be a microwave reduced pressure drying device equipped with a pressure reducing means, and the relative humidity of the environment in which the raw material composition is placed can be controlled by the pressure reducing means provided in the microwave reduced pressure drying device.

In one embodiment, the production method of the present invention further includes a step of controlling the temperature and relative humidity of the environment in which the composition containing a pharmaceutically acceptable salt of citric acid, a hydrate thereof, or a mixture thereof, preferably potassium citrate monohydrate and sodium citrate dihydrate, is placed.

The moisture content of the raw material composition decreases over time due to microwave irradiation, and after a certain period of time, the moisture content becomes, for example, less than 6.0% by mass or less than 7.5% by mass. However, in the present specification, a composition other than the target composition containing a pharmaceutically acceptable salt of citric acid or a hydrate thereof, or a mixture thereof, preferably potassium citrate monohydrate and sodium citrate dihydrate and having a moisture content of 4.0% by mass or less may be referred to as a raw material composition for the convenience of explanation. That is, in the present specification, there are cases where the term raw material composition refers to a composition containing a pharmaceutically acceptable salt of citric acid, a hydrate thereof, or a mixture thereof, preferably potassium citrate monohydrate and sodium citrate dihydrate, and having a moisture content of, for example, 6.0 to 12.0% by mass, 7.5 to 11.0% by mass, 7.5 to 10.0% by mass, or 7.5 to 8.5% by mass, and there are cases where the term raw material composition refers to a composition, as an object to be irradiated with microwaves, containing a pharmaceutically acceptable salt of citric acid or a hydrate thereof, or a mixture thereof, preferably potassium citrate monohydrate and sodium citrate dihydrate, and having a moisture content of less than 6.0% by mass or less than 7.5% by mass when irradiated with microwaves (provided that the target composition containing a pharmaceutically acceptable salt of citric acid or a hydrate thereof, or a mixture thereof, preferably potassium citrate monohydrate and sodium citrate dihydrate, and having a moisture content of 4.0% by mass or less is excluded).

In one embodiment, by controlling the temperature of the environment in which the raw material composition is placed, the moisture reduction efficiency of the raw material composition can be increased, and the decomposition and/or changes in the chemical structure of components of the raw material composition can be suppressed. For example, citric acid may be convened to aconitic acid by intramolecular dehydration at or above 175° C. Sodium citrate dihydrate may lose water of crystallization and change to an anhydride at 150° C. Therefore, the temperature of the raw material composition irradiated with the microwaves is preferably controlled to be 50° C., or higher and 80° C., or lower at the initial stage of the microwave irradiation (in the present specification, may be referred to as a "first section") (for example, 22 minutes from the start of the microwave irradiation, and preferably 18 minutes from the start of the microwave irradiation), and the temperature is controlled, in the subsequent stage (in the present specification, may be referred to as a "second section"), that is, after 22 minutes after the start of the microwave irradiation, to be 90° C., or higher and lower than 175° C. preferably 100° C., or higher and 150° C., or lower, more preferably 100° C., or higher and 120° C., or lower, and still more preferably 110° C., so that the moisture reduction efficiency of the raw material composition can be increased, and the decomposition and/or changes in the chemical structure of components of the raw material composition can be suppressed.

The temperature of the raw material composition irradiated with the microwaves can be controlled, for example, by controlling the microwave output and/or by controlling another controllable heat source (in the present specification, may be referred to as a heating means).

In one embodiment, the set output of the microwave irradiation unit is 2 kW or more and 24 kW or less, preferably 2 kW or more and 12 kW or less, more preferably 2 kW or more and 6 kW or less, still more preferably 4 kW or more and 6 kW or less, and can be changed over time within this range, and when the present production method is carried out in a continuous manner, it can be changed over time, or can be set for each microwave irradiation unit installed in a row.

Further, in another embodiment, the microwave output is 0.05 kW/kg or more and 2 kW/kg or less, preferably 0.2 kW/kg or more and 2 kW/kg or less, more preferably 0.2 kW/kg or more and 1 kW/kg or less, still more preferably 0.24 kW/kg or more and 1 kW/kg or less, particularly preferably 0.24 kW/kg or more and 0.5 kW/kg or less, and can be changed over time within this range, and when the present production method is carried out in a continuous manner, it can e changed over time, or can be set for each microwave irradiation unit installed in a row.

In one embodiment, the moisture reduction efficiency of the raw material composition can be increased by controlling the relative humidity of the environment in which the raw material composition is placed. In the present production method, by irradiating the raw material composition with microwaves, moisture evaporated from the raw material composition tends to increase the relative humidity of the environment in which the raw material composition is placed. Therefore, it is considered preferable to exhaust the moisture evaporated from the raw material composition to the outside of the environment in which the raw material composition is placed, and to control the relative humidity of the environment so as not to increase. However, in the present production method, surprisingly, by controlling the relative humidity of the environment to be a relatively high relative humidity of 80% RH or higher and 100% RH or lower at the initial stage of the microwave irradiation (in the present specification, may be referred to as a "first section") (for example, before the microwave irradiation or 22 minutes, preferably 18 minutes from the start of the microwave irradiation), and by controlling the relative humidity of the environment to 10% RH or higher and 90% RH or lower in the subsequent stage (in the present specification, may be referred to as a "second section") (that is, after 22 minutes after the start of the microwave irradiation), as compared to the case where the relative humidity is not controlled to be high at the initial stage, the moisture content of the raw material composition can be efficiently reduced, the moisture content of the target composition can be further reduced, and the composition having excellent hygroscopic properties can be obtained.

In one embodiment, when relatively high relative humidity which is preferred in the first section is not achieved, only by the moisture evaporated from the raw material composition by irradiating the raw material composition with microwaves, due to the small mass of the raw material composition, it is also possible to supply steam to forcibly achieve relatively high relative humidity.

In one embodiment, the initial stage (first section) of the microwave irradiation may be before the microwave irradiation or may be 22 minutes, preferably 18 minutes, more preferably 11 minutes, still more preferably 9 minutes, still more preferably 6 minutes, still more preferably 4 minutes, still more preferably 3 minutes, and still more preferably 2 minutes from the start of the microwave irradiation. Further, in another embodiment, it may be before the microwave irradiation or may be at least 1 minute from the start of the microwave irradiation.

In one embodiment, the relative humidity of the environment after the initial stage (second section) is preferably controlled to 20% RH or higher and 80% RH or lower, more preferably 25% RH or higher and 60% RH or lower, still more preferably 25% RH or higher and 50% RH or lower, and particularly preferably 25% RH or higher and 40% RH or lower.

The relative humidity of the environment can be controlled by the air exhaustion control of the environment.

In one embodiment, the ending time of the microwave irradiation can be determined by monitoring the moisture content of the raw material composition, and the microwave irradiation can be ended usually from 10 to 70 minutes, preferably from 15 to 45 minutes, and more preferably from 22 to 40 minutes.

The target composition can be obtained by ending the microwave irradiation. When the microwave irradiation is finished, the powder of the target composition may be aggregated. Since the target composition itself is used as a medicament or as a pharmaceutical raw material, the aggregated target composition is preferably crushed and sized. The crushing can be performed using a crusher known per se, and the sizing can be performed using a sizer known per se. In one embodiment, as the above sizer, for example, a sizer equipped with a 16 mesh sieve can be used.

In one embodiment, the raw material composition may contain anhydrous citric acid, and may further contain the above additive, preferably partially pregelatinized starch.

By containing the partially pregelatinized starch, it is possible to suppress partial decomposition of the raw material composition due to the uneven irradiation of the microwaves during the microwave irradiation, and to suppress the aggregation of the target composition after the microwave irradiation. Furthermore, when the raw material composition is conveyed by blowing air after mixing each component of the raw material composition, such conveyance can be facilitated.

Each component of the raw material that may be used in the present production method, that is, a pharmaceutically acceptable salt of citric acid or a hydrate thereof, more specifically potassium citrate monohydrate, sodium citrate dihydrate, anhydrous citric acid, and the above additives can be produced by methods known per se, or can be obtained as commercially available products.

<Microwave Drying Device>

In one embodiment, the production method of the present invention can be carried out using a microwave drying device. An example of the microwave drying device will be described below.

A microwave drying device 1 shown in FIG. 1 is provided with a microwave irradiation chamber 60 having a microwave irradiation unit 40, and a conveying means 30 such as a belt conveyor is provided so that an object, to be conveyed can pass through the microwave irradiation chamber. The microwave irradiation chamber is provided with one or more freely openable and closable exhaust ports (sometimes referred to as dampers) 70. It is preferable to include a plurality of microwave irradiation chambers, and in the example of the device in FIG. 1, the microwave irradiation chambers are called zones, and there are four microwave irradiation chambers, that is, four zones. Each zone can be configured to be connected. In that case, in each zone, an object to be irradiated can be irradiated with microwaves in a continuous manner by the conveying means 30 such as a belt conveyor, but each zone is preferably partitioned by partition walls (60*a*, 61*a*, and 62*a*), and as a result, each zone can function as an independent microwave irradiation chamber (60, 61, 62 and 63). Each zone is provided with a microwave irradiation unit (40, 41, 42 and 43), and the output of each microwave irradiation unit can be individually controlled by a control section 50. In addition, it is configured so that each zone has one or more freely openable and closable exhaust ports (sometimes called dampers) (70, 71, 72, and 73), and the air exhaustion in each zone can be individually controlled. In addition, the microwave drying device 1 can be provided with a heat source (not shown) separate from the microwave irradiation unit (in the present specification, sometimes referred to as a heating means). It can be configured so that the heat source includes a control section (not shown), and the temperature of each zone can be controlled by controlling the heating by the heat source as well as controlling the microwave irradiation.

A V-type mixer 10 and a pulverizer/classifier 20 are connected to the microwave drying device 1 by pipes 10*a* and 20*a*. The microwave drying device 1 is configured so that a raw material composition 100 supplied from the pulverizer/classifier 20 through the pipe 20*a* is placed on the belt conveyor 30, and conveyed in the direction from the microwave irradiation chamber 60 to the microwave irradiation chamber 61, while passing through each microwave irradiation chamber. Further, it is configured so that a target composition that haw been irradiated with microwaves is charged into a crusher 80, crushed as necessary, and recovered as a target composition 101.

The width of the conveying means, such as a belt conveyor, is preferably from 120 to 180 cm, and particularly preferably 150 cm.

Therefore, the microwave irradiation chamber is preferably configured so that the conveying means conveys an object to be conveyed through the interior of the microwave irradiation chamber, and the size in the direction orthogonal to the conveying direction of the conveying means is, for example, from 130 to 240 cm, preferably from 160 to 220 cm, and more preferably 200 cm. In addition, the microwave irradiation chamber may have a size of, for example, 80 to 160 cm, 80 to 120 cm, 85 to 160 cm, 90 to 110 cm, or 100 cm in the conveying direction of the conveying means. Therefore, as one embodiment, in the microwave drying device having four microwave irradiation chambers, the sections where the conveying means is irradiated with microwaves may be 320 to 500 cm, 320 to 480 cm, 360 to 480 cm, 360 to 440 cm, or 400 cm. Further, the volume of the microwave irradiation chamber may be from 0.7 to 3.0 $m^3$, from 0.8 to 2.5 $m^3$, from 0.9 to 2.2 $m^3$, or from 1.0 to 2.0 $m^3$. The ratio of the volume of the microwave irradiation chamber and the mass of the raw material composition to be irradiated is 5 $kg/m^3$ or more, preferably 10 $kg/m^3$ or more, and more preferably 12 kg/m or more, and if the range of the ratio is from 5 to 20 kg/nm, preferably from 10 to 16 kg/m, more preferably from 12 to 14 kg/n, and still more preferably from 12.7 to 13.5 kg/n, the adjustment of the relative humidity in the microwave irradiation chamber to a desired range using the moisture evaporated from the raw material composition by the microwave irradiation may be facilitated. Furthermore, the height of the microwave irradiation chamber (that is, the distance from the highest position in the space inside the microwave irradiation chamber to the upper surface of the conveying means, such as a belt of a belt conveyor) may be from 4 to 6 cm, and preferably 4 cm. By having such a microwave irradiation chamber, it is possible to efficiently irradiate the conveyed object with microwaves.

Each of the microwave irradiation units described above has a set output of 2 kW or more and 24 kW or less, preferably 2 kW or more and 12 kW or less, and more preferably 2 kW or more and 6 kW or less.

<Production Method Using Microwave Drying Device>

As one embodiment, the production method of the present invention includes:

a) a step of preparing a composition obtained by mixing a pharmaceutically acceptable salt of citric acid or a hydrate thereof, or a mixture thereof, and optionally another component, that are placed in a normal state;

b) a step of placing the composition on a conveying means in a microwave drying device;

c) a step of conveying the composition placed on the conveying means to a microwave irradiation chamber provided in the microwave drying device; and d) a step of continuously irradiating the composition conveyed to the microwave irradiation chamber with microwaves.

The production method of the present invention may further include:

e) the step of preparing a composition includes mixing by a mixer; and f) the step of placing on a conveying means includes conveyance by blowing air into a pipe connecting the mixer and the microwave drying device.

The above step a) can be carried out, for example, by charging, into the V-type mixer 10 connected to the microwave drying device 1 shown in FIG. 1, a pharmaceutically acceptable salt of citric acid or a hydrate thereof, or a mixture thereof, preferably potassium citrate monohydrate and sodium citrate dihydrate, and optionally another component, and mixing each component (the above step e)), conveying a mixed composition to the pulverizer/classifier 20 through the pipe 10*a*, and pulverizing and/or classifying by the pulverizer/classifier 20. The pulverized and/or classified raw material composition can be conveyed by blowing air into the pipe 20*a* (the above step f)), and the conveyed raw material composition 100 is deposited and placed so as to form a layer having a height of about 3 cm (for example, from 2.0 to 3.5 cm) and a width of about 130 cm (for example, from 128 to 132 cm) onto the upper portion of the belt conveyor 30 (the above step b)).

By sequentially conveying the raw material composition 100 placed on the belt conveyor 30 from the microwave irradiation chamber 60 to the microwave irradiation chamber 63 provided in the microwave drying device (the above step c)), the raw material composition 100 can be irradiated with microwaves in a continuous manner (the above step d)).

As one embodiment, in each zone of the microwave drying device 1 (corresponding to the microwave irradiation chambers (60, 61, 62, and 63)), the set output of the microwaves is preferably controlled to 4 kW or more and within 6 kW. The temperature of the raw material composition 100 irradiated with microwaves is preferably controlled, for example, from 43 to 50° C. in the microwave irradiation chamber 60, from 70 to 80° C. in the microwave irradiation chamber 61, from 110 to 115° C. in the microwave irradiation chamber 62, and to 110° C. in the microwave irradiation chamber 63.

As one embodiment, in each zone of the microwave drying device 1 (corresponding to the microwave irradiation chambers (60, 61, 62, and 63)), the microwave output is preferably 0.05 kW/kg or more and 2 kW/kg or less, more preferably 0.2 kW/kg or more and 2 kW/kg or less, still more preferably 0.2 kW/kg or more and 1 kW/kg or less, still more preferably 0.24 kW/kg or more and 1 kW/kg or less, and particularly preferably 0.24 kW/kg or more and 0.5 kW/kg or less. Here, the mass of an object to be irradiated in each zone is represented by the mass of the conveyed raw material composition 100 present in each zone, and can be obtained from the volume of the raw material composition 100 present in each zone and the specific gravity of this raw material composition.

As one embodiment, the set output and temperature of each zone of the microwave drying device 1 are preferably controlled to be 5 kw and 43° C. in the microwave irradiation chamber 60, 4 kw and 70° C. in the microwave irradiation chamber 61, 4 kw and 115° C. in the microwave irradiation chamber 62, and 5 kw and 110° C. in the microwave irradiation chamber 63. Further, an object to be dried in the above embodiment is preferably a composition containing potassium citrate monohydrate ($C_6H_5K_3O_7 \cdot H_2O$), sodium citrate dihydrate ($C_6H_5Na_3O_7 \cdot 2H_2O$) and anhydrous citric acid.

As one embodiment, the set output and temperature of each zone of the microwave drying device 1 are preferably controlled to be: 5 kw and 50° C. in the microwave irradiation chamber 60, from 4 to 6 kw and from 75 to 80° C. in the microwave irradiation chamber 61, 5 kw and 110° C. in the microwave irradiation chamber 62, and 5 kw and 110° C. in the microwave irradiation chamber 63, and more preferably controlled to be: 5 kw and 50° C.: in the microwave irradiation chamber 60, from 4 to 6 kw and 75° C. in the microwave irradiation chamber 61, 5 kw and 110° C. in the microwave irradiation chamber 62, and 5 kw and 110° C. in the microwave irradiation chamber 63. In addition, an object to be dried in the above embodiment is preferably a composition containing potassium citrate monohydrate ($C_6H_5K_3O_7 \cdot H_2O$), sodium citrate dihydrate ($C_6H_5Na_3O_7 \cdot 2H_2O$), anhydrous citric acid and an additive (for example, partially pregelatinized starch).

As one embodiment, the exhaust port 70 of the microwave irradiation chamber 60 is closed so as to control the relative humidity to be relatively high in the initial stage of the microwave irradiation, and the exhaust port 71 of the microwave irradiation chamber 61 can be closed, or be opened, as desired. The microwave irradiation chambers 62 and 63 have exhaust ports 72 and 73 opened in order to reduce the relative humidity in the microwave irradiation chambers.

The speed of the belt conveyor 30 is preferably from 68 to 110 (mm/min), more preferably from 90 to 110 mm/min), and still more preferably from 100 to 110 (mm/min), and the total width of the plurality of microwave irradiation chambers (that is, the length of the section where the raw material composition is irradiated with microwaves in the traveling direction of the belt conveyor) may be from 320 to 500 cm, from 320 to 480 cm, from 360 to 480 cm, from 360 to 440 cm, or 400 cm.

<Method for Drying Citrate-Containing Composition>

One embodiment of the present invention is a method of drying a composition containing a pharmaceutically acceptable salt of citric acid or a hydrate thereof, or a mixture thereof, preferably potassium citrate monohydrate and sodium citrate dihydrate, by beating, and may be a drying method including a step of controlling the temperature and relative humidity of the environment in which the composition is placed to temporarily increase the moisture content of the composition at the initial stage of the heating.

A heating means in the above drying method is not particularly limited. Here, the heating means may be any heat source that has or can generate a temperature higher than the ambient temperature, and examples thereof include an infrared heater, a gas burner, a heating medium (for example, air, oil, and water are exemplified as a medium), and an electromagnetic wave (for example, microwave) irradiation unit known per se, or a combination thereof.

As one embodiment, for example, by heat radiation or heat conduction or heat transfer from the infrared heater, gas burner, or heating medium, the composition containing a pharmaceutically acceptable salt of citric acid or a hydrate thereof, or a mixture thereof, preferably potassium citrate monohydrate and sodium citrate dihydrate, can be heated, and in another embodiment, the composition containing a pharmaceutically acceptable salt of citric acid or a hydrate thereof, or a mixture thereof, preferably potassium citrate monohydrate and sodium citrate dihydrate, can be heated by radiant heating by irradiating microwaves from a microwave irradiation unit.

The drying method of the present invention is characterized in that the temperature and relative humidity of the environment in which the composition is placed at the initial stage of the heating are controlled to temporarily increase the moisture content of the composition.

As one embodiment, for example, when the method of the heating is a method by heat radiation, or by heat conduction or heat transfer from a heat source such as an infrared heater, a gas burner, or a heating medium, it is preferable to temporarily increase the moisture content of the composition, which is an object to be dried, by controlling the temperature of the environment at the initial stage of the heating to be 50° C. or higher and 65° C., or lower and the relative humidity to be 45% RH or higher and 60% RH or lower.

As one embodiment, for example, when the method of the heating is a method by radiant heating by irradiating microwaves from a microwave irradiation unit, it is preferable to temporarily increase the moisture content of the composition, which is an object to be dried, by controlling the temperature of the environment at the initial stage of the heating to be 50° ° C. or higher and 80° C. or lower and the relative humidity to be 80% RH or higher and 1000% RH or lower.

In one embodiment, the increase in the moisture content usually means that, when the moisture content of the composition before drying is, for example, from 7.5 to 8.5% by mass with respect to the total mass of the composition, it is preferably temporarily increased to 9.0% by mass or more, preferably increased to 9.0 to 11.5% by mass in a broad sense, preferably increased to 9.0 to 10.0% by mass in a narrower sense, and preferably increased to 9.0 to 9.5% by mass in an even narrower sense. As described above, by temporarily increasing the moisture content of the composition, which is an object to be dried, the object to be dried can be dried more efficiently than a method that does not involve such a step, and the moisture content of the object to be dried can be further reduced. In the present specification, the term "drying" means that the moisture content of the object to be dried may be 4% by mass or less, preferably 3.0% by mass or less, more preferably 2.5% by mass or less, still more preferably 2.0% by mass or less, and particularly preferably 1.7% by mass or less, with respect to the total mass of the object to be dried, and the lower limit value thereof may be 0.0% by mass.

In one embodiment, when the method of the heating is a method by heat radiation, or by heat conduction or heat transfer from a heat source such as an infrared heater, a gas burner, or a heating medium, as described above, by maintaining the temperature and relative humidity of the environment at, the initial stage of the heating after temporarily increasing the moisture content of the composition, the object to be dried can be dried efficiently. The drying time is, for example, from 20 to 28 hours, preferably from 22 to 26 hours, and more preferably 24 hours when the citrate-containing composition as an object to be dried is, for example, from 1 to 100 g.

In one embodiment, when the method of the heating is a method by radiant heating by irradiating microwaves from a microwave irradiation unit, by controlling the temperature of the environment in which the composition is placed to be 90° C., or higher and less than 175° C., and the relative humidity to be 10% RH or higher and 90% RH or lower, the object to be dried can be dried efficiently. As the microwave irradiation conditions, the conditions described in the above production method can be applied, and the drying time may be, for example, when the citrate-containing composition as an object to be dried has a thickness of 25 to 40 mm, from 15 to 120 minutes, preferably from 15 to 80 minutes, more preferably from 15 to 40 minutes, still more preferably from 20 to 30 minutes, and still more preferably 25 minutes.

In one embodiment, when a method by radiant heating using microwaves is employed as the method of the heating, the microwave output may be, for example, in a broad sense, 2 kW/kg or less, preferably 1 kW/kg or less, and more preferably 0.5 kW/kg or less. Although the lower limit value of the microwave output is not particularly limited, for example, if it is 0.05 kW/kg or more, the moisture content of the object to be irradiated can be efficiently reduced. Therefore, as the microwave output range, examples thereof include 0.05 to 2 kW/kg, or 0.20 to 2 kW/kg, examples of narrower range include 0.2 to 1 kW/kg, or 0.20 to 0.5 kw/kg, examples of even narrower range include 0.24 to 1 kW/kg, 0.24 to 0.5 kw/kg or 0.20 to 0.4 kw/kg, and examples of the narrowest range include 0.20 to 0.30 kw/kg and 0.24 to 0.30 kw/kg, and the object to be dried can be efficiently dried under any of these conditions.

The citrate-containing composition dried by employing the drying method of the present invention may be a citrate-containing composition having the specific hygroscopic properties.

<Pharmaceutical Preparation>

A composition containing a pharmaceutically acceptable salt of citric acid, a hydrate thereof, or a mixture thereof, preferably potassium citrate monohydrate and sodium citrate dihydrate, and having a moisture content of 400 by mass or less (hereinafter may be referred to as a target composition, and a pharmaceutically acceptable salt of citric acid, a hydrate thereof, or a mixture thereof, preferably potassium citrate monohydrate and sodium citrate dihydrate may be referred to as an active ingredient), which is obtained by the production method of the present invention or dried by employing the drying method of the present invention, can be used as a raw material for formulating pharmaceutical products.

The above target composition may be prepared as a medicament by mixing with the pharmaceutically acceptable additive, if desired. Such formulations may be formulations such as tablets, powdered drugs, capsules, suspensions, injections, or suppositories. The above medicament is administered to humans or other mammals orally or parenterally, and examples of parenteral administration include intravenous administration, subcutaneous administration, intramuscular administration, intra-articular administration, transmucosal administration, transdermal administration, nasal administration, rectal administration, intrathecal administration, intraperitoneal administration, and topical administration.

Tablets will be described in more detail below.

In one embodiment, the tablet may contain a pharmaceutically acceptable additive commonly used in the pharmaceutical field, in addition to the active ingredient (for example, potassium citrate monohydrate and sodium citrate dihydrate). Examples of such an additive include an excipient, a binder, a disintegrant, a fluidizer, a flavoring agent, a lubricant, a pH adjuster, a surfactant, a stabilizer, and a perfume.

The content of the active ingredient in the tablet may be from 10 to 95% by mass, preferably from 50 to 90% by mass, more preferably from 60 to 90% by mass, and still more preferably from 70 to 85% by mass, with respect to the tablet.

Examples of the excipient that can be used for the above tablet include sugars such as lactose (for example, lactose hydrates and anhydrous lactose), glucose, sucrose, fructose, and maltose, sugar alcohols such as erythritol, sorbitol, maltitol, xylitol, and D-mannitol, starches (for example, corn starch, potato starch, rice starch, and wheat starch, crystalline cellulose, magnesium aluminometasilicate, anhydrous calcium phosphate, precipitated calcium carbonate, calcium silicate, calcium lactate and ethyl cellulose, and crystalline cellulose is particularly preferred.

The content of the excipient in the tablet may be from 1 to 95% by mass, preferably from 1 to 50% by mass, more preferably from 1 to 30% by mass, still more preferably from 1 to 10% by mass, and most preferably from 1 to 7% by mass, with respect to the tablet.

Examples of the binder that may be used for the above tablet include hydroxypropyl cellulose, hydroxypropyl methylcellulose, polyvinylpyrrolidone, dextrin, methylcellulose, polyvinyl alcohol, sodium alginate, aminoalkyl methacrylate copolymers, polyethylene glycol, pregelatinized starch (for example, partially pregelatinized starch), agar and gelatin, and hydroxypropyl cellulose is particularly preferred.

The content of the binder in the tablet may be from 0.1 to 30% by mass, preferably from 0.1 to 10% by mass, more preferably from 0.1 to 3% by mass, still more preferably from 0.1 to 1% by mass, and most preferably from 0.2 to 0.8% by mass, with respect to the tablet.

Examples of the disintegrant that may be used for the above tablet include croscarmellose sodium, carmellose calcium, sodium carboxymethyl starch, low-substituted hydroxypropyl cellulose, crospovidone, starches (for example, wheat starch, corn starch, and partially pregelatinized starch) and carmellose, and partially pregelatinized starch is particularly preferred.

The content of the disintegrant in the tablet may be from 0.3 to 20% by mass, preferably from 1 to 10% by mass, more preferably from 3 to 10% by mass, and still more preferably from 3 to 6% by mass, with respect to the tablet.

Examples of the fluidizer that may be used for the above tablet include light anhydrous silicic acid, tale, and magnesium aluminometasilicate.

The content of the fluidizer in the tablet may be from 0.03 to 3% by mass, preferably from 0.1 to 3% by mass, and more preferably from 0.3 to 3% by mass, with respect to the tablet.

Examples of the flavoring agent that may be used for the above tablet include acidulants such as malic acid, acetic acid, tartaric acid, fumaric acid and ascorbic acid, and sweeteners such as sodium saccharin, dipotassium glycyrrhizinate, aspartame (registered trademark), stevia, thaumatin and sucralose.

The content of the flavoring agent in the tablet may be from 0.03 to 3% by mass, preferably from 0.1 to 3% by mass, and more preferably from 0.3 to 3% by mass, with respect to the tablet.

Examples of the lubricant that may be used for the above tablet include magnesium stearate, calcium stearate, talc, light anhydrous silicic acid, sucrose fatty acid esters, carnauba wax, macrogol and sodium stearyl fumarate, and magnesium stearate is particularly preferred.

The content of the lubricant in the tablet may be from 0.1 to 30% by mass, preferably from 0.1 to 10% by mass, more preferably from 0.3 to 5% by mass, and still more preferably from 0.5 to 3% by mass, with respect to the tablet.

Examples of the pH adjuster that may be used for the above tablet include phosphates (for example, sodium dihydrogen phosphate and potassium dihydrogen phosphate), carbonates (for example, magnesium carbonate and sodium carbonate), tartrates, fumarates, acetates and amino acid salts.

The content of the pH adjuster in the tablet may be from 0.1 to 30% by mass, preferably from 0.3 to 10% by mass, and more preferably from 1 to 5% by mass, with respect to the tablet.

Examples of the surfactant that may be used for the above tablet include sodium lauryl sulfate, polysorbate, sucrose fatty acid esters, polyoxyethylene hydrogenated castor oil, polyoxyl stearate, macrogol and poloxamer.

The content of the surfactant in the tablet may be from 0.01 to 3% by mass, preferably front 0.03 to 1% by mass, and more preferably from 0.03 to 0.5% by mass, with respect to the tablet.

Examples of the stabilizer that may be used for the above tablet include anhydrous citric acid, malic acid, acetic acid, tartaric acid, maleic acid, ascorbic acid, sodium edetate, and tocopherol.

The content of the stabilizer in the tablet may be from 0.01 to 30% by mass, preferably from 0.1 to 30% by mass, and more preferably from 1 to 20% by mass, with respect to the tablet.

Examples of the perfume that may be used for the above tablet include citrus-based perfumes of lemon, orange, grapefruit and the like, peppermint, spearmint and menthol, and it can be contained in the tablet in an appropriate amount (for example, from 0.01 to 1% by mass, and more preferably from 0.01 to 0.1% by mass, with respect to the tablet).

The total content of the active ingredients and the pharmaceutically acceptable additives in the tablet, does not exceed 100% by mass with respect to the tablet.

The tablet contains the above components and can be an uncoated tablet without a coating layer, or can be a film-coated tablet with a coating layer. The content of the coating layer can be appropriately set by those skilled in the art, and may be, for example, front 0.1 to 10% by mass with respect to the uncoated tablet. The coating layer may appropriately contain a plasticizer, a colorant, a brightener, and the like, in addition to the coating base.

Examples of the coating base that may be used for the above tablet include hypromellose, hydroxypropyl cellulose, hydroxypropyl methylcellulose, ethyl cellulose, cellulose acetate phthalate, methacrylic acid copolymers and polyvinylpyrrolidone, and hypromellose is particularly preferred. The content of the coating base in the tablet provided by the present invention may be from 0.01 to 10% by mass, and preferably from 0.3 to 3% by mass, with respect to the tablet.

Examples of the coating plasticizer that may be used for the above tablet include triethyl citrate, medium-chain fatty acid triglycerides, triacetin, glycerin, propylene glycol and polyethylene glycol (for example. Macrogol 6000), and Macrogol 6000 is particularly preferred. The content of the coating plasticizer in the tablet may be from 0.01 to 1% by mass, and preferably from 0.03 to 3% by mass, with respect to the tablet.

Examples of the coating colorant that may be used for the above tablet include titanium oxide, yellow ferric oxide, iron sesquioxide, black iron oxide, food blue No. 2 and food blue No. 2 aluminum lake. The content of the coating colorant in the tablet may be from 0.01 to 1% by mass, and preferably from (0.03 to 3% by mass, with respect to the tablet.

Examples of the coating brightener that may be used for the above tablet include carnauba wax. The content of the coating brightener in the tablet may be from 0.0001 to 0.1% by mass, and preferably from 0.001 to 0.01% by mass, with respect to the tablet.

A method for producing the above tablet may include a mixing step of mixing the target composition obtained by the production method of the present invention with an additive, if desired, a granulation step, a tableting step and/or a coating step.

The mixing step may include a step of mixing the active ingredient with an additive such as an excipient, a stabilizer, a disintegrant and/or a binder. In addition, it may further include a step of mixing a mixture containing the active ingredient and an additive with a lubricant, a flavoring agent and/or a perfume agent prior to the tableting step. The mixing can be performed using a V-type mixer, a W-type mixer, a container mixer, a tumbler mixer, a stirring mixer, or the like.

The granulation step can be performed by a granulation method known in the pharmaceutical field. Examples of the granulation method include a dry granulation method, a wet granulation method and a fluidized bed granulation method.

As one embodiment, the mixture obtained in the mixing step and the granulated material obtained in the granulation step may be appropriately pulverized and/or sieved to obtain a mixture or a granulated material having a desired particle size. The pulverization can be performed, for example, with a pulverizer known in the pharmaceutical field, such as a ball mill, a jet mill, and a hammer mill. The sieving can be performed using a 16 mesh sieve (opening: 1,000 μm), a 32 mesh sieve (opening: 500 μm) or the like.

The tableting step can be performed by a tableting method known in the pharmaceutical field. Examples of the tableting method include a direct compression method, a dry compression method, a wet compression method and an external lubrication compression method. In particular, when using the target composition obtained by the production method of the present invention, a direct compression method can be employed. Further, for example, the mixture or granulated material obtained in the above steps can be tableted using a tableting machine known in the pharmaceutical field, such as a single punch tableting machine and a rotary tableting machine. When using a single punch tableting machine, a rotary tableting machine, or the like, a tableting pressure of 1 kN to 30 kN can be employed.

The coating step can be performed by a method known in the pharmaceutical field. For example, it can be carried out by spray-coating a coating liquid containing a coating base, a plasticizer, a colorant, a brightener and the like as appropriate on the outside of the uncoated tablet.

In one embodiment, the above tablet can be produced by: mixing and tableting an active ingredient, an excipient (for example, lactose, D-mannitol, crystalline cellulose and/or glucose), a binder (for example, hydroxypropyl cellulose (HPC), gelatin and/or polyvinyl pyrrolidone (PVP)), a stabilizer (for example, anhydrous citric acid), a disintegrant (for example, starch (for example, partially pregelatinized starch) and/or carboxymethylcellulose calcium (CMC-Ca) and a lubricant (for example, magnesium stearate) to obtain an uncoated tablet; and forming, outside the uncoated tablet, a coating layer containing a coating base (for example, hypromellose, hydroxypropyl cellulose, hydroxypropyl methylcellulose and/or PVP) and a plasticizer (for example, triethyl citrate and/or Macrogol 6000), a colorant. (for example, iron sesquioxide and/or titanium oxide) and a brightener (for example, carnauba wax).

In one embodiment, the hardness of the obtained tablet may be from 10 to 200N, and preferably from 30 to 150N.

Further, a powdered drug can be produced by mixing the target composition obtained by the production method of the present invention with an additive, if desired, and subjecting the composition to spray granulation using a spray granulation drying apparatus (for example, New Marumerizer NQ-230, manufactured by Fuji Paudal Co., Ltd.). Examples of the spray liquid used in the spray granulation include ethanol and water, and ethanol is preferred. The spray granulation can be carried out by setting the air volume of the spray granulator from 0.8 to 2.0 $m^3$/min, preferably from 1.0 to 1.34 $m^3$/min, and setting the blast temperature during granulation from 20 to 40° C., preferably from 26 to 33° C., and the blast temperature during drying from 60 to 80° C., preferably 75° C., so that the temperature of the granulated material is from 20 to 50° C., preferably from 26 to 42° C.

Next, the present invention will be described in more detail with reference to Examples, but the present invention is not limited to these Examples. In the following Examples and Test Examples, "%" represents "% by mass" unless otherwise specified.

EXAMPLES

Example 1

Production of citrate-containing composition using microwave drying device (1) A target citrate-containing composition was produced using a microwave dryer (NJF6406) manufactured by New Japan Radio Co., Ltd. In the above microwave dryer, a microwave irradiation section had four zones (microwave irradiation chambers) Z-1 to Z-4 in order from the upstream side of conveyance by a belt conveyor, and was provided with a microwave irradiation unit for each zone. The microwave output of each zone was set, in order from the zone Z-1, to 5 kW, 4 kW, 5 kW and 5 kW, and the conveying speed of the belt conveyor was set to 100 to 110 mm/min. Further, the opening degree of a damper (exhaust port) of each zone was set, in order from the zone Z-1, to 0 (fully closed), 10 mm, 10 mm and 10 mm. A raw material composition containing potassium citrate monohydrate ($C_4H_5K_3O_7{\cdot}H_2O$), sodium citrate dihydrate ($C_6H_5Na_3O_7{\cdot}2H_2O$), anhydrous citric acid, and partially pregelatinized starch, obtained by mixing with a V-type mixer (V-300; manufactured by Tokuju Corporation), and pulverized and classified with a pulverizer/classifier (ACM pulverizer (ACM-10); manufactured by Hosokawa Micron Corporation), was supplied on a belt conveyor so that the raw material composition formed a layer having a thickness of about 3 cm and a width of about 130 cm. The moisture content of the above raw material composition was a normal moisture content as shown in Test Example 1. In addition, in each zone, the temperature of the raw material compound was set, in order from the zone Z-1, to 50° C., 75° C., 110° C., and 110° C. A composition containing potassium citrate monohydrate ($C_6H_5K_3O_7{\cdot}H_2O$), sodium citrate dihydrate ($C_6H_5Na_3O_7{\cdot}2H_2O$), anhydrous citric acid and partially pregelatinized starch and having a target moisture content of 1.22 to 1.59% by mass was obtained by treatment with the above dryer, crushing aggregated raw material compounds with a crusher, and sizing with a sizer (HRG-125; manufactured by Hata Tekkosho Co., Ltd.) under the condition of 16 mesh (opening; 1 mm). Table 1 shows the composition of the raw material composition and the moisture content of each lot after drying. It should be noted that the moisture content was measured by a method of ending the measurement when reaching 0.05%/min or less) under automatic stop conditions of 5 g/180° C., using a heating and drying type moisture meter (MX-50, manufactured by A & D Co., Ltd.). Further, the average particle size (D50) of the composition produced in the same manner after the above particle size adjustment was 100 μm or less in all cases (10 μm or less in all cases). The results are shown in Table 2.

TABLE 1

| Lot | A | B | C |
|---|---|---|---|
| Potassium citrate monohydrate (kg) | 98.040 | 98.040 | 98.040 |
| Sodium citrate dihydrate (kg) | 88.880 | 88.880 | 88.880 |
| Anhydrous citric acid (kg) | 29.000 | 29.000 | 29.000 |
| Partially pregelatinized starch (kg) | 9.600 | 9.600 | 9.600 |
| Moisture content after drying (%) | 1.22 | 1.59 | 1.23 |

TABLE 2

| Lot | D | E | F |
|---|---|---|---|
| Potassium citrate monohydrate (kg) | 98.040 | 98.040 | 98.040 |
| Sodium citrate dihydrate (kg) | 88.880 | 88.880 | 88.880 |
| Anhydrous citric acid (kg) | 29.000 | 29.000 | 29.000 |
| Partially pregelatinized starch (kg) | 9.600 | 9.600 | 9.600 |
| Particle size after sizing: D10 (μm) | 1.19 | 1.20 | 1.22 |
| Particle size after sizing: D50 (μm) | 9.39 | 9.37 | 9.48 |
| Particle size after sizing: D90 (μm) | 29.40 | 29.37 | 29.70 |

Example 2

Production of Citrate-Containing Composition Using Microwave Drying Device (2)

A composition containing potassium citrate monohydrate ($C_4H_5K_3O_7{\cdot}H_2O$), sodium citrate dihydrate ($C_6H_5Na_3O_7{\cdot}2H_2O$), anhydrous citric acid and partially pregelatinized starch and having a target moisture content of 1.50 to 1.60% by mass was obtained in the same manner as in Example 1, with the exception that the conveying speed of the belt conveyor in Example 1 was set to 90 mm/min, and the temperature of the raw material compound in each zone was set, in order from the zone Z-1, to 50° C., 80° C., 1110° C., and 110° C. it should be noted that the moisture content was measured by a Karl Fischer method (colormetric titration method). Table 3 shows the composition of the raw material composition and the moisture content of each lot after drying.

TABLE 3

| Lot | G | H | I |
| --- | --- | --- | --- |
| Potassium citrate monohydrate (kg) | 122.55 | 122.55 | 147.06 |
| Sodium citrate dihydrate (kg) | 111.0 | 111.10 | 133.32 |
| Anhydrous citric acid (kg) | 36.25 | 36.25 | 43.50 |
| Partially pregelatinized starch (kg) | 12.00 | 12.00 | 14.40 |
| Moisture content after drying (%) | 1.50 | 1.60 | 1.58 |

Example 3

Production of Citrate-Containing Composition Using Microwave Drying Device (3)

A target citrate-containing composition was produced using a microwave dryer (MCH-24000) manufactured by Micro Denshi Co., Ltd. In the above microwave dryer, a microwave irradiation section had four zones (microwave irradiation chambers) Z-1 to Z-4 in order from the upstream side of conveyance by a belt conveyor, and was provided with a microwave irradiation unit for each zone. The microwave output of each zone was set, in order from the zone Z-1, to 5 kW, 5 kW, 6 kW and 5 kW, and the conveying speed of the belt conveyor was set to 110 mm/min. Further, the opening degree of a damper (exhaust port) of each zone was set, in order from the zone Z-1, to 0% (fully closed), 0%, 5%, and 10% with respect to the fully opened state. A raw material composition containing potassium citrate monohydrate ($C_6H_5K_3O_7 \cdot H_2O$), sodium citrate dihydrate ($C_6H_5Na_3O_7 \cdot 2H_2O$), anhydrous citric acid, and partially pregelatinized starch, obtained by mixing with a V-type mixer, and pulverized and classified with a pulverizer/classifier (ACM pulverizer (ACM-15H); manufactured by Hosokawa Micron Corporation), was supplied on a belt conveyor so that the raw material composition formed a layer having a thickness of about 2.5 cm and a width of about 130 cm. The moisture content of the above raw material composition was a normal moisture content as shown in Test Example 1. In addition, in each zone, the temperature of the raw material compound was set, in order from the zone Z-1, to 50° C., 75° C., 110° C. and 110° C. A composition containing potassium citrate monohydrate ($C_6H_5K_3O_7 \cdot H_2O$), sodium citrate dihydrate ($C_6H_5Na_3O_7 \cdot H_2O$), anhydrous citric acid and partially pregelatinized starch and having a target moisture content of 1.44% by mass was obtained by treatment with the above dryer, crushing aggregated raw material compounds with a crusher, and particle size adjustment with a sizer (HRG-125V-II; manufactured by Hata Tekkosho Co., Ltd.) under the condition of 16 mesh (opening: 1 mm). It should be noted that the moisture content was measured by the same method as in Example 1. Table 4 shows the composition of the raw material composition and the moisture content after drying.

TABLE 4

| Lot | J |
| --- | --- |
| Potassium citrate monohydrate (g) | 73.530 |
| Sodium citrate dihydrate (g) | 66.660 |
| Anhydrous citric acid (g) | 21.750 |
| Partially pregelatinized starch (g) | 7.200 |
| Moisture content after drying (%) | 1.44 |

Example 4

Production of Citrate-Containing Composition Using Microwave Drying Device (4)

A composition containing potassium citrate monohydrate ($C_6H_5K_3O_7 \cdot H_2O$), sodium citrate dihydrate ($C_6H_5Na_3O_7 \cdot 2H_2O$), anhydrous citric acid and partially pregelatinized starch and having a target moisture content of 1.50% by mass was obtained in the same manner as in Example 3, with the exception that the microwave output of each zone in Example 3 was set, in order from the zone Z-1, to 5 kW, 5 kW, 5 kW, and 5 kW. It should be noted that the moisture content was measured by the same method as in Example 1. Table 5 shows the composition of the raw material composition and the moisture content after drying.

TABLE 5

| Lot | K |
| --- | --- |
| Potassium citrate monohydrate (g) | 73.530 |
| Sodium citrate dihydrate (g) | 66.660 |
| Anhydrous citric acid (g) | 21.750 |
| Partially pregelatinized starch (g) | 7.200 |
| Moisture content after drying (%) | 1.50 |

Example 5

(1) Drying of Citric Acid-Containing Composition by Microwave Irradiation (Batch Type)

A composition obtained by blending potassium citrate monohydrate ($C_6H_5K_3O_7 \cdot H_2O$), sodium citrate dihydrate ($C_6H_5Na_3O_7 \cdot 2H_2O$) and anhydrous citric acid so that the molar ratio thereof was 2:2:1 was dried using a microwave dryer (NJE6607) manufactured by New Japan Radio Co., Ltd. 4.7 kg of the above composition was placed in a polypropylene container so as to have a thickness of 30 to 35 mm, and installed in the microwave dryer. By setting the microwave output (oscillation frequency: 2.450±30 MHz) to 2.0 kW and setting the temperature of the above composition to 148 to 150° C., drying was carried out at normal pressure until water vapor was generated, and after the generation of water vapor, the water vapor was discharged by reducing the pressure to 750 hPa, and drying was performed for a total of 100 minutes. The moisture content of the composition before drying was 8.16% by mass with respect to the mass of the composition, and the moisture content of the composition after drying was 1.87% by mass with respect, to the mass of the composition. It should be noted that the moisture content, was measured by a Karl Fischer method (coulometric titration method).

(2) Hygroscopic Stability Test

Figure 2:
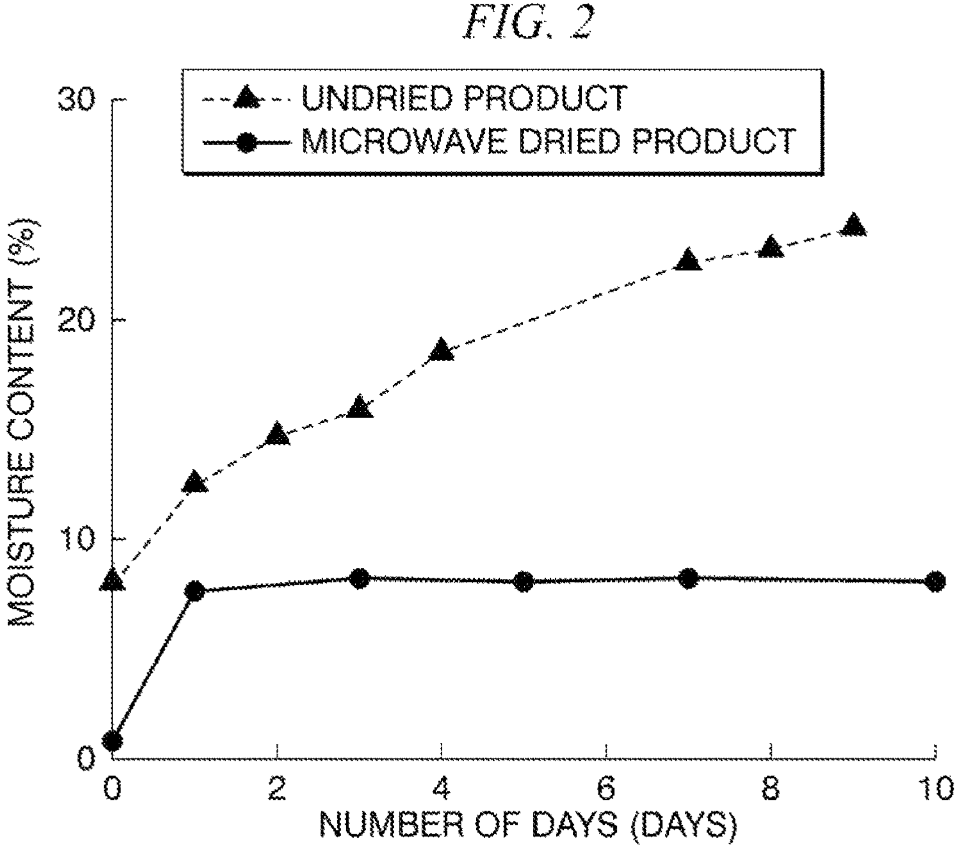
FIG. 2 is a graph comparing hygroscopic stability of a composition produced by the production method of the present invention and hygroscopic stability of a composition mixed in a normal state.

According to the above method-s (1) to (4), the dried composition was pulverized in a mortar, 1 g of a sample was collected in a weighing bottle and allowed to stand in an environment of 25° C. and a relative humidity of 75% RH, and the amount of moisture absorption was measured over time. The results are shown in FIG. 2. In the composition to which the above drying method was applied, the moisture content 10 days after the completion of microwave irradiation was 1.5 times or less the moisture content 2 days after the completion of the irradiation.

Test Example 1

Moisture Content of Citric Acid-Containing Composition Before Drying

A composition obtained by blending potassium citrate monohydrate ($C_6H_5K_3O_7{\cdot}H_2O$), sodium citrate dihydrate ($C_6H_5Na_3O_7{\cdot}2H_2O$) and anhydrous citric acid so that the molar ratio thereof was 2:2:1 was prepared in a normal state.

The above composition was prepared by mixing in a plastic bag or with a V-type mixer for 10 minutes and then pulverizing with a pin mill (160Z type, total pin).

Each of the scales and the moisture contents after preparation (before drying) are shown in Table 6. It should be noted that the moisture content was measured by a Karl Fischer method (coulometric titration method).

TABLE 6

| Lot | L | M | N | O | P | Q |
|---|---|---|---|---|---|---|
| Scale (kg) | 5 | 5 | 5 | 6 | 6 | 6 |
| Moisture content (%) | 8.20 | 8.20 | 8.20 | 7.98 | 8.00 | 7.84 |

The composition of potassium citrate monohydrate ($C_6H_5K_3O_7{\cdot}H_2O$), sodium citrate dihydrate ($C_6H_5Na_3O_7{\cdot}2H_2O$) and anhydrous citric acid had a moisture content of 7.84 to 8.20% by mass when not dried in a normal state.

Test Example 2

Figure 3:
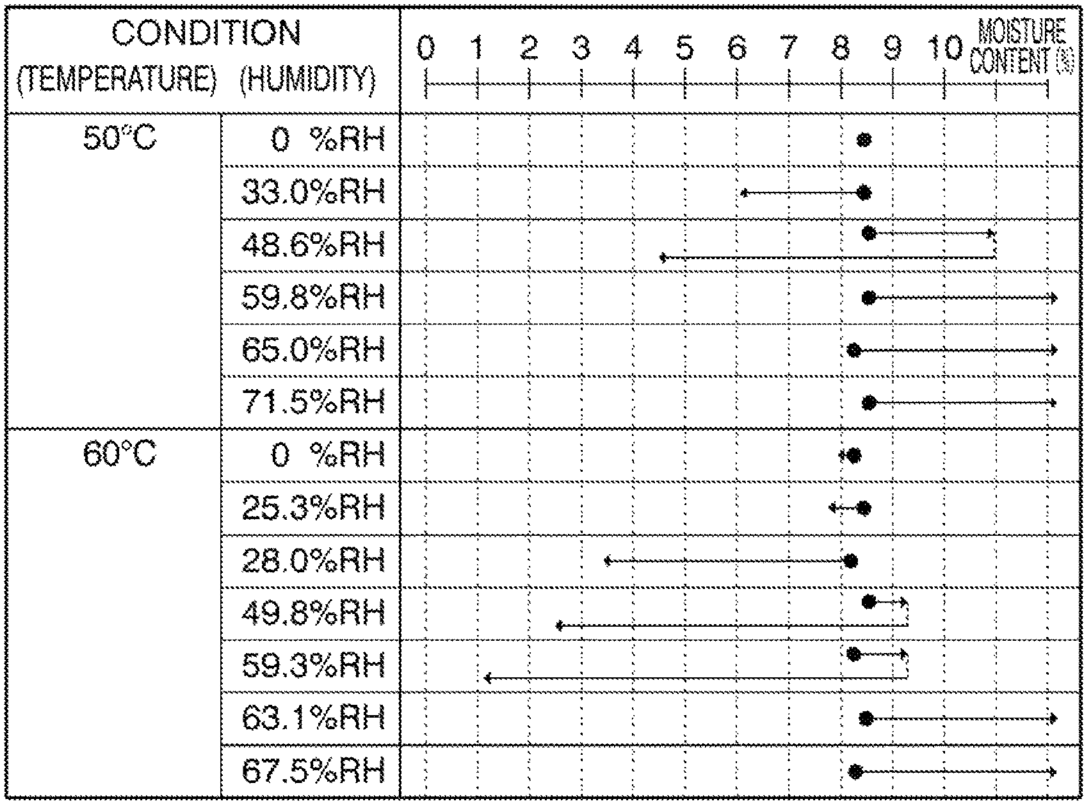
FIG. 3 is a diagram showing the results of a drying test of a citric acid-containing composition using a shelf type dryer in Test Example 1.

Drying of Citric Acid-Containing Composition by Constant Temperature and Humidity Bath A composition obtained by blending potassium citrate monohydrate ($C_6H_5K_3O_7{\cdot}H_2O$), sodium citrate dihydrate ($C_6H_5Na_3O_7{\cdot}2H_2O$) and anhydrous citric acid so that the molar ratio thereof was 2:2:1 was prepared. The above composition was pulverized using a sample mill (screen: 0.5 mmφ, clearance: 0.5 mm). 1 g of each pulverized sample was collected in a weighing bottle, and each weighing bottle was allowed to stand under the environment shown in Table 7 using a constant temperature and humidity bath, and the fluctuation of the moisture content of each sample was measured for 1 to 8 days. The results are shown in FIG. 3. As a result, in the sample placed in an environment of 60° C. and 59.3% RH, the moisture content temporarily increased to about 9.3% by mass, and then the moisture content finally decreased at most to 1.2% by mass. On the other hand, in the samples allowed to stand in a drier environment such as 60° C., and 0% RH or 25.3% RH, the moisture content did not temporarily increase, and the final moisture content was about 8.0% by mass or 7.8% by mass. It should be noted that the moisture content was measured by a Karl Fischer method (coulometric titration method).

TABLE 7

| Temperature (° C.) | Relative humidity (% RH) |
|---|---|
| 50 | 0 |
| | 33.0 |
| | 48.6 |
| | 59.8 |
| | 65.0 |
| | 71.5 |
| 60 | 0 |
| | 25.3 |
| | 28.0 |
| | 49.8 |
| | 59.3 |
| | 63.1 |
| | 67.5 |

Test Example 3

Aggregation Suppression Effect of Raw Material Composition Before Drying 24 g or 48 g of partially pregelatinized starch (PCS-PC10, manufactured by Asahi Kasei Chemicals Corporation) was added to 1,080 g of a mixture obtained by blending potassium citrate monohydrate ($C_6H_5K_3O_7{\cdot}H_2O$)), sodium citrate dihydrate ($C_6H_5Na_3O_7{\cdot}2H_2O$) and anhydrous citric acid so that the molar ratio thereof was 2:2:1, and mixed in a plastic bag for 5 minutes. Then, the resulting mixture was pulverized using a pin mill (160Z, manufactured by Powrex Corporation) to obtain a raw material composition. 500 g of each composition was allowed to stand at room temperature for 30 minutes or overnight, and the retention rates were compared with an 8-mesh sieve. The standing treatment was carried out in an environment of 24° C., and 46% RH.

The composition to which 24 g of partially pregelatinized starch was added had an 8-mesh retention rate of 3.2% by mass after standing for 30 minutes and an 8-mesh retention rate of 4.4% by mass after standing overnight. Further, the composition to which 48 g of partially pregelatinized starch was added had an 8-mesh retention rate of 0.6% by mass after standing for 30 minutes, and an 8-mesh retention rate of 0.8% by mass after standing overnight. All the compositions tended to suppress aggregation after being allowed to stand for 30 minutes, and the effect was maintained even after being allowed to stand overnight.

Further, it was possible to convey any raw material composition by blowing air through the pipe.

In order to examine the conditions of the production method according to the present invention, the following tests were further conducted. The following tests were carried out by performing continuous drying under four production conditions in a specific microwave irradiation chamber in order to examine the conditions of a continuous type microwave drying device.

Test Examples 4-1 to 4-3

Examination of Set Temperature of Device and Moisture Content

In order to examine the set temperature range that allows drying by microwave irradiation, Test Examples 4-1 to 4-3 were carried out under the conditions described in Tables 8 to 10, respectively. The raw material composition containing potassium citrate monohydrate ($C_6H_5K_3O_7{\cdot}H_2O$), sodium citrate dihydrate ($C_6H_5Na_3O_7{\cdot}2H_2O$), anhydrous citric acid and partially pregelatinized starch used in Example 1 was used as an object to be tested. Each table shows the moisture content of the composition after drying under each drying condition in each test. The moisture content after drying was measured in the same manner as in Example 1 using a heating and drying type moisture meter (MX-50, manufactured by A &. D Co., Ltd.).

TABLE 8

Test Example 4-1

| Drying condition | Equipment used<br>Microwave continuous heating equipment (MCH-M240BB)<br>1 | <br><br>2 | <br><br>3 | <br><br>4 |
|---|---|---|---|---|
| Microwave output (kW/kg) | 0.5 | 0.5 | 0.5 | 0.5 |
| Set temperature (° C.) | 50 | 75 | 110 | 110 |
| Damper (%/open) | 0 | 0 | 10 | 10 |
| Thickness of composition supply layer (mm) | 30 | 30 | 30 | 30 |
| Charged amount | 1,000 g/3 trays | 1,000 g/3 trays | 1,000 g/3 trays | 1,000 g/3 trays |
| Drying time (min) | 10 | 10 | 10 | 20 |
| Boiler | Present | Present | Absent | Absent |
| Relative humidity (%/RH) | 100 | 100 | Left to chance | Left to chance |
| Composition surface temperature (° C.) | 50.8 to 64.1 | 55.2 to 77.4 | 68.6 to 96.1 | 98.0 to 103.4 |
| Moisture content of composition after drying (%) | 9.69 | 8.15 | 3.73 | 1.76 |

TABLE 9

Test Example 4-2

| Drying condition | Equipment used<br>Microwave continuons heating equipment (MCH-M240EB)<br>1 | <br><br>2 | <br><br>3 | <br><br>4 |
|---|---|---|---|---|
| Microwave output (kW/kg) | 0.5 | 0.5 | 0.5 | 0.5 |
| Set temperature (° C.) | 50 | 75 | 90 | 90 |
| Damper (%/open) | 0 | 0 | 10 | 10 |
| Thick of composition supply layer (mm) | 30 | 30 | 30 | 30 |
| Charged amount | 1,000 g/3 trays | 1,000 g/3 trays | 1,000 g/3 trays | 1,000 g/3 trays |
| Drying time (min) | 10 | 17.5*[1] | 20*[1] | 20 |
| Boiler | Present | Present | Absent | Absent |
| Relative humidity (%/RH) | 100 | 100 | Left to chance | Left to chance |
| Composition surface temperature (° C.) | 26.0 to 52.3 | 50.7 to 80.1 | 75.0 to 105.3 | 101.5 to 112.3 |
| Moisture content of composition after drying (%) | 9.94 | 7.11 | 2.43 | 2.29 |

*[1]Compared to Test Example 4-1, time was extended due to low composition temperature.

TABLE 10

Test Example 4-3

| Drying condition | Equipment used<br>Microwave continuous heating equipment (MCH-M240EB)<br>1 | <br><br>2 | <br><br>3 | <br><br>4 |
|---|---|---|---|---|
| Microwave output (kW/kg) | 0.5 | 0.5 | 0.5 | 0.5 |
| Set temperature (° C.) | 50 | 75 | 100 | 100 |
| Damper (%/open) | 0 | 0 | 10 | 10 |
| Thickness of composition supply layer (mm) | 30 | 30 | 30 | 30 |
| Charged amount | 1,000 g/3 trays | 1,000 g/3 trays | 1,000 g/3 trays | 1,000 g/3 trays |
| Drying time (min) | 10 | 10 | 20*[1] | 20 |
| Boiler | Present | Present | Absent | Absent |
| Relative humidity (%/RH) | 100 | 100 | Left to chance | Left to chance |
| Composition surface temperature (° C.) | 66.1 | 52.0 to 80.8 | 71.2 to 110.8 | 107.0 to 117.8 |

TABLE 10-continued

| Test Example 4-3 | | | | |
|---|---|---|---|---|
| | Equipment used Microwave continuous heating equipment (MCH-M240EB) | | | |
| Drying condition | 1 | 2 | 3 | 4 |
| Moisture content of composition er drying (%) | 10.06 | 7.60 | 2.57 | 1.40 |

*[1]Compared to Test Example 4-1, time was extended due to low composition surface temperature.

Test Example 5

Measurement of Moisture Content by Simultaneous Thermogravimetric-Differential Thermal Analyzer (TG-DTA)

The moisture content of each of the undried raw material composition used in Test Examples 4-1 to 4-3 and the composition obtained after drying under the drying condition 4 in Test Examples 4-1 to 4-3 was measured using a simultaneous thermogravimetric-differential thermal analyzer (Thermo plus BVO TO 8120 (manufactured by Rigaku Corporation)) under the following measurement conditions.

Measurement Condition:

Rate of temperature increase: 20.0° C./min

Measurement temperature range: 30 to 300° C.

Measurement atmosphere: air

Gas flow rate: 500 mL/min

Sample weight: 5 mg

The results are shown in Table 11.

TABLE 11

| Test Example 5 | Drying system | Decreased amount of hydrated water of sodium citrate (%) | Decreased amount of hydrated water of potassium citrate (%) |
|---|---|---|---|
| Undried product | — | 5.62 | 1.99 |
| Composition of Test Example 4-1 | Continuous | 1.65 | 0.77 |
| Composition of Test Example 4-2 | Continuous | 4.68 | — |
| Composition of Test Example 4-3 | Continuous | 1.92 | 1.03 |

From the above results, it was found that, in all the compositions of Test Examples 4-1 to 4-3, the water of crystallization of the hydrate desorbed. From the above results, it was found that drying proceeded efficiently at a drying temperature of 100° C., or higher. It should be noted that the moisture content of the undried product (the undried raw material composition used in Test Examples 4-1 to 4-3) was 11.4% when it was measured by the same method as in Example 1, and by adding 1.99% thereto which was the amount of water of crystallization of potassium citrate hydrate, the moisture content including water of adhesion was obtained as 13.39%.

Test Examples 6-1 to 6-4

Examination of Suitable Range of Drying Method Using Microwaves

Although drying was performed with a microwave output of 0.5 kW/kg per unit mass of an object to be irradiated, a set temperature of 110° C., and a drying time of 20 minutes, with 1 kg of the above object, when the volume of the irradiation chamber was about 0.765 $m^3$, the moisture content of the composition after drying did not reach 2% or less, probably because a high relative humidity could not be obtained only by the moisture evaporated from the above object. Therefore, drying was performed after a humidification operation. While paying attention to the treatment, time so that the object to be tested did not ignite, the microwave output per unit mass was varied from 0.5 to 3 kW/kg, and operations of Test Examples 6-1 to 6-4 were carried out under the conditions described in Tables 12 to 15, respectively. The raw material composition containing potassium citrate monohydrate ($C_6H_5K_3O_7{\cdot}H_2O$), sodium citrate dihydrate ($C_6H_5Na_3O_7{\cdot}2H_2O$), anhydrous citric acid and partially pregelatinized starch used in Example 1 was used as an object to be tested. Each table shows the moisture content of the composition after drying under each drying condition in each test. The moisture content after drying was measured in the same manner as in Example 1 using a heating and drying type moisture meter (MX-50, manufactured by A & D Co., Ltd.).

TABLE 12

| Test Example 6-1 | | |
|---|---|---|
| | Equipment used Microwave batch heating equipment (MBH-M120NT) | |
| Drying condition | 1 | 2 |
| Microwave output (kW/kg) | 0.5 | 0.5 |
| Set temperature (° C.) | 110 | 110 |
| Damper (%/open) | 0 | 50 |
| Thickness of composition supply layer (mm) | 30 | 30 |
| Charged amount | 1,000 g/3 trays | 1,000 g/3 trays |
| Drying time (min) | 10 | 25 |
| Boiler | Present | Absent |
| Relative humidity (%/RH) | 100 | Left to chance |
| Composition surface temperature (° C.) | 94.9 | 94.9 to 119.2 |
| Moisture content of composition after drying (%) | — | 1.94 |

TABLE 13

| Text Example 6-2 | | |
|---|---|---|
| | Equipment used Microwave batch heating equipment (MBH-M120NT) | |
| Drying condition | 1 | 2 |
| Microwave ontput (kW/kg) | 1 | 1 |
| Set temperaure (° C.) | 110 | 110 |
| Damper (%/open) | 0 | 50 |
| Thickness of composition supply layer (mm) | 30 | 30 |
| Charged amount | 1,000 g/3 trays | 1,000 g/3 trays |
| Drying time (min) | 10 | 10 |
| Boiler | Present | Absent |
| Relative humidity (%/RH) | 100 | Left to chance |
| Composition surface temperature (° C.) | 10.2 to 110.0 | 110.0 to 128.8 |
| Moisture content of composition after drying (%) | — | 1.40 |

TABLE 14

| Test Example 6-3 | | | |
|---|---|---|---|
| | Equipment used Microwave batch heating equipment (MBH-M120NT) | | |
| Drying condition | 1 | | 2 |
| Microwave output (kW/kg) | — | 2 | —*2 |
| Set temperature (° C.) | 110 | 110 | 10 |
| Damper (%/open) | 0 | 0 | 50 |
| Thickness of composition supply layer (mm) | 30 | 30 | 30 |
| Charged amount | 1,000 g/3 trays | 1,000 g/3 trays | 1,000 g/3 trays |
| Drying time (min) | 5 | 5 | 10 |
| Boiler | Present | Present | Absent |
| Relative humidity (%/RH) | 100 | 100 | Left to chance |
| Composition surface temperature (° C.) | 170.0 | | 110.6 to 170.0 |
| Moisture content of composition after drying (%) | — | | 1.08 |

*2Drying was performed without using microwaves due to high composition surface temperature.

TABLE 15

| Test Example 6-4 | | | |
|---|---|---|---|
| | Equipment used Microwave batch heating equipment (MBH-M120NT) | | |
| Drying condition | 1 | | 2 |
| Microwave output (kW/kg) | — | 3 | 3 |
| Set temperature (° C.) | 110 | 110 | 110 |
| Damper (%/open) | 0 | 0 | 50 |
| Thickness of composition supply layer (mm) | 0 | 30 | 30 |
| Charged amount | 1,000 g/3 trays | 1,000 g/3 trays | 1,000 g/3 trays |
| Drying time (min) | 9 | 1 | 0.5*3 + 0.5 |
| Boiler | Present | Present | Absent |
| Relative humidity (%/RH) | 100 | 100 | Left to chance |

TABLE 15-continued

| Test Example 6-4 | | |
|---|---|---|
| | Equipment used Microwave batch heating equipment (MBH-M120NT) | |
| Drying condition | 1 | 2 |
| Composition surface temperature (° C.) | 15.5 to 148.9 | (1) 100.0 to 148.9<br>(2) 127.6 to 148,9 |
| Moisture content of composition after drying (%) | — | (1) 4.23<br>(2) 3.28 |

*3Surface temperature was measured every 30 seconds in order to carefully evaluate the increase of surface temperature.

As a result, of the above tests, the moisture content of the composition after drying was 2% or less at microwave outputs of 0.5, 1, and 2 kW/kg, but it was 3.28% at a microwave output of 3 kW/kg (Table 15). It is thought that this is because the surface temperature of the composition increased faster at a microwave output of 3 kW/kg, as compared to those at microwave outputs of 0.5, 1, and 2 kW/kg, so that the increase in the temperature of the object to be tested as a whole (inside) was not enough.

Test Example 7

Measurement of Moisture Content by Simultaneous Thermogravimetric-Differential Thermal Analyzer (TO-DTA)

The moisture content of each of the undried raw material composition used in Test Examples 6-1 to 6-3 and the composition obtained after drying under the drying condition 2 in Test Examples 6-1 to 6-3 was measured using a simultaneous thermogravimetric-differential thermal analyzer (Thermo plus EVO TG 8120 (manufactured by Rigaku Corporation)) under the same conditions as the measurement conditions described in Test Example 5. The results are shown in Table 16.

TABLE 16

| Test Example 7 | Drying system | Decreased amount of hydrated water of sodium citrate (%) | Decreased amount of hydrated water of potassium citrate (%) |
|---|---|---|---|
| Undried product | — | 5.62 | 1.99 |
| Composition of Test Example 6-1 | Batch | 1.75 | 1.34 |
| Composition of Test Example 6-2 | Batch | 2.40 | 1.33 |
| Composition of Test Example 6-3 | Batch | 1.78 | 0.57 |

From the above results, it was found that, the water of crystallization of sodium citrate and potassium citrate hydrates efficiently desorbed as a result of drying within a microwave output range of 0.5 to 2 kW/kg, t should be noted that the moisture content of the undried product (the undried raw material composition used in Test Examples 6-1 to 6-3) was 11.4% when it was measured by the same method as in Example 1, and by adding 1.99% thereto which was the amount of water of crystallization of potassium citrate hydrate, the moisture content including water of adhesion was obtained as 13.39%.

Test Examples 8-1 and 8-2

Examination of Composition Ratio of Sodium Citrate and Potassium Citrate

The effects on drying due to differences in the composition ratio of sodium citrate and potassium citrate in the composition were examined. The composition ratio (molar ratio) of sodium citrate and potassium citrate of the raw material composition used in Test Example 6-1 was changed to a ratio of sodium citrate:potassium citrate=0:1 (Test Example 8-1) and a ratio of sodium citrate:potassium citrate=3:1 (Test Example 8-2), and operation, of Test Examples 8-1 and 8-2 were carried out under the conditions described in Tables 17 and 18, respectively. Each table shows the moisture content of the composition after drying under each drying condition in each test. The moisture content after drying was measured using a heating and drying type moisture meter (MX-50, manufactured by A & D Co., Ltd.). It should be noted that when the moisture contents of the undried raw material compositions used in Test Examples 8-1 and 8-2 were measured in the same manner as in Example 1 using a heating and drying type moisture meter (MX-50, manufactured by A & D Co., Ltd.), they were 7.49% and 11.28%, respectively. Considering the amount of water of crystallization of potassium citrate hydrate from the results of Test Examples 5 and 7, the moisture contents of the undried products of Test Examples 8-1 and 8-2 were 11.47%, and 12.28%, respectively.

TABLE 17

Text Example 8-1

| | Equipment used Microwave batch heating equipment (MBH-M120NT) | |
|---|---|---|
| Drying condition | 1 | 2 |
| Microwave output (kW/kg) | 0.5 | 0.5 |
| Set temperature (° C.) | 110 | 110 |
| Damper (%/open) | 0 | 50 |
| Thickness of composition supply layer (mm) | 30 | 30 |
| Charged amount | 1,000 g/3 trays | 1,000 g/3 trays |
| Drying time (min) | 10 | 20 |
| Boiler | Present | Absent |
| Relative humidity (%/RH) | 100 | Left to chance |
| Composition surface temperature (° C.) | 17.4 to 16.0 | 116.0 to 131.2 |
| Moisture content of composition after drying (%) | — | 0.75 |

TABLE 18

Test Example 8-2

| | Equipment used Microwave batch heating equipment (MBH-M120NT) | |
|---|---|---|
| Drying condition | 1 | 2 |
| Microwave output (kW/kg) | 0.5 | 0.5 |
| Set temperature (° C.) | 110 | 110 |
| Damper (%/open) | 0 | 50 |
| Thickness of composition supply layer (mm) | 30 | 30 |
| Charged amount | 1,000 g/3 trays | 1,000 g/3 trays |
| Drying time (min) | 15 | 15 + 15*6 |
| Boiler | Present | Absent |
| Relative humidity (%/RH) | 100 | Left to chance |
| Composition surface temperature (° C.) | 125.1 | (1) 125.1 to 132.2<br>(2) 113.0 to 140.7 |
| Moisture content of composition after drying (%) | — | (1) 3.03<br>(2) 1.04 |

*6Redrying 15 min

INDUSTRIAL APPLICABILITY

According to the present invention, it is possible to provide an efficient method for producing a citrate-containing composition containing a pharmaceutically acceptable salt of citric acid, a hydrate thereof, a mixture thereof, or the like and having a low moisture content.

REFERENCE SIGNS LIST

1: Microwave drying device
10: V-type mixer
20: Pulverizer/classifier
30: Belt conveyor
40, 41, 42, 43: Microwave irradiation unit
50: Control section
60, 61, 62, 63: Microwave irradiation chamber
70, 71, 72, 73: Exhaust port
80: Crusher
100: Raw material composition
101: Target composition

The invention claimed is:

1. A production method for a composition comprising a pharmaceutically acceptable salt of citric acid or a hydrate thereof, or a mixture thereof and having a moisture content of 4.0% by mass or less, the production method comprising: a step of irradiating a composition containing a pharmaceutically acceptable salt of citric acid, a hydrate thereof, or a mixture thereof with microwaves, wherein the pharmaceutically acceptable salt of citric acid or the hydrate thereof, or the mixture thereof is an alkali metal salt of citric acid or a hydrate thereof, or a mixture thereof.

2. The production method according to claim 1, further comprising:

a step of controlling a temperature and relative humidity of an environment in which said composition comprising a pharmaceutically acceptable salt of citric acid or a hydrate thereof, or a mixture thereof is placed.

3. The production method according to claim 1, wherein the pharmaceutically acceptable salt of citric acid or the hydrate thereof, or the mixture thereof is potassium citrate or a hydrate thereof, sodium citrate or a hydrate thereof, or a mixture thereof.

4. The production method according to claim 1, wherein the pharmaceutically acceptable salt of citric acid or the hydrate thereof, or the mixture thereof is potassium citrate monohydrate ($C_6H_5K_3O_7 \cdot H_2O$), sodium citrate dihydrate ($C_6H_5Na_3O_7 \cdot 2H_2O$), or a mixture thereof.

5. The production method according to claim 2, wherein said step of controlling the temperature and relative humidity comprises provision of a first section in which a temperature of said composition irradiated with said microwaves is controlled so that the relative humidity is 80% RH or higher and 100% RH or lower from start of the irradiation with said microwaves.

6. The production method according to claim 5, wherein said step of controlling the temperature and relative humidity includes provision of a second section in which the relative humidity is controlled to 10% RH or higher and 90% RH or lower after passing through said first section.

7. The production method according to claim 5, wherein said first section is controlled to be 50° C. or higher and 80° C. or lower.

8. The production method according to claim 1, wherein a temperature of said composition irradiated with said microwaves is 90° C. or higher and lower than 175° C.

9. The production method according to claim 1, wherein a temperature of said composition irradiated with said microwaves is 100° C. or higher and 120° C. or lower.

10. The production method according to claim 1, wherein a temperature of said composition irradiated with said microwaves is 110° C.

11. The production method according to claim 1, wherein an output of said microwaves is 0.05 kW/kg or more and 2 kW/kg or less.

12. The production method according to claim 1, wherein said composition further comprises an additive.

13. The production method according to claim 1, wherein said composition further comprises anhydrous citric acid.

14. The production method according to claim 1, wherein said composition further comprises partially pregelatinized starch.

15. The production method according to claim 1, further comprising:

a) a step of preparing a composition obtained by mixing said pharmaceutically acceptable salt of citric acid or a hydrate thereof, or a mixture thereof, and optionally another component, that are placed in a normal state;

b) a step of placing said composition on a conveying means in a microwave drying device;

c) a step of conveying the composition placed on said conveying means to a microwave irradiation chamber provided in said microwave drying device; and d) a step of continuously irradiating the composition conveyed to said microwave irradiation chamber with microwaves.

16. The production method according to claim 15, wherein e) said step of preparing the composition comprises mixing by a mixer; and f) said step of placing on a conveying means comprises conveyance by blowing air into a pipe connecting said mixer and said microwave drying device.

17. The production method according to claim 15, wherein controlling of the relative humidity is performed by opening and/or closing an exhaust port provided in said microwave irradiation chamber.

18. The production method according to claim 1, further comprising:

a) a step of preparing a composition obtained by mixing said pharmaceutically acceptable salt of citric acid or a hydrate thereof, or a mixture thereof, and optionally another component, that are placed in a normal state;

b1) a step of placing said composition in a microwave reduced pressure drying device; and c1) a step of irradiating said placed composition with microwaves.

19. The production method according to claim 18, wherein controlling of the relative humidity is performed by a pressure reducing means provided in said microwave reduced pressure drying device.

20. A drying method for a composition comprising a pharmaceutically acceptable salt of citric acid, a hydrate thereof, or a mixture thereof by heating, the drying method comprising: a step of controlling a temperature and relative humidity of an environment in which said composition is placed to temporarily increase a moisture content of said composition at an initial stage of said heating, wherein the pharmaceutically acceptable salt of citric acid or the hydrate thereof, or the mixture thereof is an alkali metal salt of citric acid or a hydrate thereof, or a mixture thereof.

21. The drying method according to claim 20, wherein the pharmaceutically acceptable salt of citric acid or the hydrate thereof, or the mixture thereof is potassium citrate or a hydrate thereof, sodium citrate or a hydrate thereof, or a mixture thereof.

22. The drying method according to claim 20, wherein the pharmaceutically acceptable salt of citric acid or the hydrate thereof, or the mixture thereof is potassium citrate monohydrate ($C_6H_5K_3O_7 \cdot H_2O$), sodium citrate dihydrate ($C_6H_5Na_3O_7 \cdot 2H_2O$), or a mixture thereof.

23. The drying method according to claim 20, wherein a method of said heating is a method by heat radiation, heat conduction or heat transfer from a heat source, and the temperature of the environment at the initial stage of the heating is 50° C. or higher and 65° C. or lower, and the relative humidity is 45% RH or higher and 60% RH or lower.

24. The drying method according to claim 20, comprising a step of maintaining the temperature and relative humidity of the environment at the initial stage of said heating after temporarily increasing the moisture content of said composition.

25. The drying method according to claim 20, wherein a method of said heating is a method of radiant heating by microwave irradiation, and the temperature of the environment at the initial stage of the heating is 50° C. or higher and 80° C. or lower, and the relative humidity is 80% RH or higher and 100% RH or lower.

26. The drying method according to claim 25, comprising a step of controlling the temperature of the environment in which said composition is placed to 90° C. or higher and lower than 175° C., and the relative humidity to 10% RH or higher and 90% RH or lower after temporarily increasing the moisture content of said composition.

27. A microwave irradiated composition comprising a pharmaceutically acceptable salt of citric acid or a hydrate thereof, or a mixture thereof, wherein said composition has a characteristic that when said composition is stored in an environment at a temperature of 25° C. and a relative humidity of 75% RH, a moisture content 10 days after the end of said irradiation is 1.5 times or less a moisture content 2 days after the end of said irradiation, wherein the pharmaceutically acceptable salt of citric acid or the hydrate thereof, or the mixture thereof is an alkali metal salt of citric acid or a hydrate thereof, or a mixture thereof.

28. The composition according to claim 27, wherein the pharmaceutically acceptable salt of citric acid or the hydrate thereof, or the mixture thereof is potassium citrate or a hydrate thereof, sodium citrate or a hydrate thereof, or a mixture thereof.

29. The composition according to claim 27, wherein the pharmaceutically acceptable salt of citric acid or the hydrate thereof, or the mixture thereof is potassium citrate monohydrate ($C_6H_5K_3O_7 \cdot H_2O$), sodium citrate dihydrate ($C_6H_5Na_3O_7 \cdot 2H_2O$), or a mixture thereof.

30. A tablet comprising the composition according to claim 27.

31. A production method for a composition comprising a pharmaceutically acceptable salt of citric acid or a hydrate thereof, or a mixture thereof, and in which a total content of the pharmaceutically acceptable salt of citric acid or the hydrate thereof, or the mixture thereof does not exceed 100% by mass with respect to a total mass of solid content of the pharmaceutically acceptable salt of citric acid or the hydrate thereof, or the mixture thereof, which is not irradiated with microwaves, the production method comprising a step of irradiating a composition containing a pharmaceutically acceptable salt of citric acid, a hydrate thereof, or a mixture thereof with microwaves, wherein the pharmaceutically acceptable salt of citric acid or the hydrate thereof, or the mixture thereof is alkali metal salts of citric acid or a hydrate thereof, or a mixture thereof.

* * * * *